US011597947B2

(12) United States Patent
Kong et al.

(10) Patent No.: US 11,597,947 B2
(45) Date of Patent: Mar. 7, 2023

(54) GENE EDITING METHOD USING VIRUS

(71) Applicant: ASC THERAPEUTICS INC., Milpitas, CA (US)

(72) Inventors: Ling-Jie Kong, Union City, CA (US); Mi Shi, Milpitas, CA (US); Hainan Chen, Milpitas, CA (US); Ruby Yanru Tsai, San Jose, CA (US)

(73) Assignee: ASC THERAPEUTICS INC., Milpitas, CA (US)

(*) Notice: Subject to any disclaimer, the term of this patent is extended or adjusted under 35 U.S.C. 154(b) by 853 days.

(21) Appl. No.: 16/475,128

(22) PCT Filed: Dec. 29, 2017

(86) PCT No.: PCT/US2017/068860
§ 371 (c)(1),
(2) Date: Jul. 1, 2019

(87) PCT Pub. No.: WO2018/126087
PCT Pub. Date: Jul. 5, 2018

(65) Prior Publication Data

US 2021/0198696 A1 Jul. 1, 2021

Related U.S. Application Data

(60) Provisional application No. 62/439,897, filed on Dec. 29, 2016.

(51) Int. Cl.

| | |
|---|---|
| ***C12N 15/87*** | (2006.01) |
| ***A61K 48/00*** | (2006.01) |
| ***C12N 9/22*** | (2006.01) |
| ***C12N 15/113*** | (2010.01) |
| ***C12N 15/861*** | (2006.01) |
| ***C12N 15/90*** | (2006.01) |
| ***C12N 15/00*** | (2006.01) |

(52) U.S. Cl.
CPC ............ *C12N 15/87* (2013.01); *A61K 48/005* (2013.01); *C12N 9/22* (2013.01); *C12N 15/113* (2013.01); *C12N 15/8616* (2013.01); *C12N 15/907* (2013.01); *C12N 2740/15011* (2013.01); *C12N 2750/14111* (2013.01); *C12Y 301/00* (2013.01); *C12Y 301/21* (2013.01)

(58) Field of Classification Search
None
See application file for complete search history.

(56) References Cited

U.S. PATENT DOCUMENTS

| | | | |
|---|---|---|---|
| 8,697,359 | B1 | 4/2014 | Zhang |
| 2003/0087817 | A1 | 5/2003 | Cox et al. |
| 2005/0026157 | A1 | 2/2005 | Baltimore et al. |
| 2014/0068797 | A1 | 3/2014 | Doudna et al. |
| 2015/0166618 | A1 | 6/2015 | Miller et al. |
| 2016/0153005 | A1 | 6/2016 | Zhang et al. |

FOREIGN PATENT DOCUMENTS

| | | | |
|---|---|---|---|
| WO | 2013169802 | A1 | 11/2013 |
| WO | 2013176772 | A1 | 11/2013 |
| WO | 2014018423 | A2 | 1/2014 |

OTHER PUBLICATIONS

Scallan et al. (Sustained phenotypic correction of canine hemophilia A using an adeno-associated viral vector, Blood, Sep. 15, 2003, vol. 102, No. 6, pp. 2031-2037).*
Rajiv Sharma et al: "In vivo genome editing of the albumin locus as a platform for protein replacement therapy", vol. 126, No. 15, Aug. 21, 2015 (Aug. 21, 2015), pp. 1777-1784, XP055547324, DOI: 10.1182/blood-2014-12-.
Communication pursuant to Article 94(3) EPC of EP 17888551.3 dated Oct. 26, 2021.
Tetsushi Sakuma et al: "MMEJ-assisted gene knock-in using TALENs and CRISPR-Cas9 with the PITCh systems", Nature Protocols, vol. 11, No. 1, Dec. 17, 2015 (Dec. 17, 2015), pp. 118-133, XP055388413, GB ISSN: 1754-2189, DOI: 10.1038/nprot.2015.140.
Yu Hisano et al: "Precise in-frame integration of exogenous DNA mediated by CRISPR/Cas9 system in zebrafish", Scientific Reports, vol. 5, Mar. 5, 2015 (Mar. 5, 2015), pp. 1-7, XP055360057, DOI: 10.1038/srep08841.
Communication pursuant to Article 94(3) EPC of the corresponding application EP 17888551.3, dated Aug. 31, 2022.
Keiichiro Suzuki et al: "In vivo genome editing via CRISPR/Cas9 mediated homology-independent targeted integration", Nature, vol. 540, No. 7631, Dec. 1, 2016 (Dec. 1, 2016), pp. 144-149, XP055737567, London, ISSN: 0028-0836, DOI: 10.1038/nature20565, figure 1b.
Jianbin Wang et al: "Highly efficient homology-driven genome editing in human T cells by combining zinc-finger nuclease mRNA and AAV6 donor delivery", Nucleic Acids Research, vol. 44, No. 3, Nov. 2, 2015 (Nov. 2, 2015), pp. e30-e30, XP055737865, ISSN: 0305-1048, DOI: 10.1093/nar/gkv1121, p. 6-p. 8; figure 5.
The extended European search report of European application No. 17888551.3, dated Oct. 16, 2020.
Keown, W. A. et al., "Methods for introducing DNA into mammalian cells", Methods in Enzymology (1990), vol. 185, pp. 527-537.

(Continued)

*Primary Examiner* — Suzanne M Noakes
*Assistant Examiner* — Jae W Lee
(74) *Attorney, Agent, or Firm* — Jun He Law Offices P.C.; Yi Zhang

(57) ABSTRACT

Provided is a method of inserting a polynucleotide sequence into a genome of a cell. The method comprises: generating a double-strand break at a target site of the genome; and introducing into the cell a virus. The virus comprises a nucleic acid comprising the polynucleotide sequence to be inserted or the complementary sequence thereof. The nucleic acid does not comprise a homologous arm or comprises very short (5~25 bp) homologous arms corresponding to the target site. Also provided herein is a composition for inserting a polynucleotide sequence into a genome of a cell. The composition comprises a site-specific nuclease capable of generating a DNA double-strand break at a target site of the genome and a virus comprising a nucleic acid comprising the polynucleotide sequence or the complementary sequence thereof.

10 Claims, 4 Drawing Sheets

Specification includes a Sequence Listing.

(56) References Cited

OTHER PUBLICATIONS

Zuker, M. et al., "Optimal computer folding of large RNA sequences using thermodynamics and auxiliary information", Nucleic Acids Research (1981), vol. 9, pp. 133-148.
Carr, P. A. et al., "Genome engineering", Nature Biotechnology (2009), vol. 27, pp. 1151-1162.
Pabo, C. O. et al., "Design and Selection of Novel Cys2His2 Zinc Finger Proteins", Annual Review of Biochemistry (2001), vol. 70, pp. 313-340.
Maeder, M. L. et al., "Rapid "Open-Source" Engineering of Customized Zinc-Finger Nucleases for Highly Efficient Gene Modification", Molecular Cell (2008), vol. 31, pp. 294-301.
Boch, J. et al., "TALEs of genome targeting", Nature Biotechnology (2011), vol. 29, pp. 135-136.
Boch, J. et al., "Breaking the Code of DNA Binding Specificity of TAL-Type III Effectors", Science (2009), vol. 326, pp. 1509-1512.
Moscou, M. J. et al., "A Simple Cipher Governs DNA Recognition by TAL Effectors", Science (2009), vol. 326, pp. 1501-1501.
Juillerat, A. et al., "Optimized tuning of TALEN specificity using non-conventional RVDs", Scientific Reports (2015), vol. 5: 8150, p. 1-7.
Christian, M. et al., "Targeting DNA Double-Strand Breaks with TAL Effector Nucleases", Genetics (2010), vol. 186, pp. 757-761.
Li, T. et al., "TAL nucleases (TALNs): hybrid proteins composed of TAL effectors and Fokl DNA-cleavage domain", Nucleic Acids Research (2011), vol. 39, pp. 359-372.
Jinek, M. et al., "A Programmable Dual-RNA-Guided DNA Endonuclease in Adaptive Bacterial Immunity", Science (2012), vol. 337, pp. 816-821.
Cong, L. et al., "Multiplex Genome Engineering Using CRISPR/Cas Systems", Science (2013), vol. 339, pp. 819-823.
Moore, J. K. et al., "Cell cycle and genetic requirements of two pathways of nonhomologous end-joining repair of double-strand breaks in *Saccharomyces cerevisiae*", Molecular and Cellular Biology (1996), vol. 16, pp. 2164-2173.
Ottaviani, D. et al., "The role of microhomology in genomic structural variation", Trends in Genetics (2014), vol. 30, pp. 85-94.
Nakade, S. et al., "Microhomology-mediated end-joining-dependent integration of donor DNA in cells and animals using TALENs and CRISPR/Cas9", Nature Communications (2014), vol. 5:5560. PDF File: p. 1-8. Abstract; p. 2, col. 1, col. 2, up para, and Fig 1a; and p. 6, col. 1, up para, col. 2, para 1, and Fig 5.
Roberts, S. A. et al., "Engineering Factor Viii for Hemophilia Gene Therapy", Journal of Genetic Syndromes & Gene Therapy (2011), vol. 1. pii: S1 006. PDF File: p. 1-16. Entire documentation, especially Abstract; p. 1, para 1; and p. 2, para 1 and para 2.
Yao, X. et al., "Homology-mediated end joining-based targeted integration using CRISPR/Cas9", Cell Research (Jun. 2017), vol. 27(6), pp. 801-814. Epub May 19, 2017. Entire documentation, especially Abstract; p. 801, col. 1; and p. 802, col. 1, top para.
International Search Report of PCT Application No. PCT/US17/68860, dated Apr. 25, 2018.

* cited by examiner

GENE EDITING METHOD USING VIRUS

CROSS-REFERENCE TO RELATED APPLICATIONS

This application claims priority to U.S. provisional patent application No. 62/439,897, filed Dec. 29, 2016, the disclosure of which is incorporated herein by reference.

SEQUENCE LISTING

A Sequence Listing in electronic format is provided as a file entitled "044903-8012US02-SL-20190807_ST25" created on Aug. 7, 2019, which is 39,542 bytes in size. The information in the electronic format of the sequence listing is incorporated by reference in its entirety.

FIELD OF THE INVENTION

The present invention generally relates to a method for gene editing using viruses.

BACKGROUND

The development of gene editing technology using engineered site-specific nuclease (e.g., CRISPR, ZFN, TALEN) opens the doors for targeted gene modification in higher organisms including human and holds great potential for gene therapy. Such gene editing technology typically depends on the nuclease to create a DNA double-strand break (DSB) and the cellular DNA repair mechanism to generate targeted mutations or gene-insertions, i.e. knock-in. Precise site-specific gene insertion usually happens through the homology directed repair (HDR) pathway, which has a low rate of recombination even in the existence of a DSB. Moreover, HDR requires a donor template to include sequences that are homologous to the flanking sequences of the DSB (homologous arms).

Viruses have been extensively used to deliver exogenous nucleic acid and therefore can be used to deliver nucleic acid reagents for gene editing. However, all viruses have limited packaging capacity in terms of the nucleic acid size. As HDR-based gene editing needs a donor template containing homologues arms, the size of the insertion fragment is limited. For example, adeno-associated virus (AAV), one of the commonly used viruses for gene delivery, only has a genome of ~4.7 kb in length, making insertion of long sequence impractical.

Therefore, there is a continuing need for developing new gene-editing technology using viruses.

SUMMARY OF INVENTION

In one aspect, the present disclosure provides a method of inserting a polynucleotide sequence into a genome of a cell. In one embodiment, the method comprises: generating a DNA double-strand break at a target location of the genome; and introducing into said cell a virus, wherein said virus comprises a nucleic acid comprising the polynucleotide sequence or the complementary sequence thereof, wherein the nucleic acid does not comprise a homologous arm corresponding to the target location.

In another aspect, the present disclosure provides a composition for inserting a polynucleotide sequence into a genome of a cell. In one embodiment, the composition comprises: site-specific nuclease capable of generating a DNA double-strand break at a target location of the genome; and a virus comprising a nucleic acid comprising the polynucleotide sequence or the complementary sequence thereof, wherein the nucleic acid does not comprise a homologous arm corresponding to the target location.

In certain embodiment, the nucleic acid comprises a microhomologous arm (5-25 bp) according to the target location.

In certain embodiments, the virus is a double strand DNA (dsDNA) virus or a virus with dsDNA intermediate during virus life cycle. The virus can be an adeno-associated virus, a retrovirus, a herpesvirus or a lentivirus.

In certain embodiments, the nucleic acid is single-strand DNA (ssDNA), double-strand DNA (dsDNA), single-strand RNA (ssRNA) or double-strand RNA (dsRNA). In certain embodiments, the polynucleotide sequence encodes B-domain deleted Factor VIII (BDD-F8). In certain embodiments, the polynucleotide sequence comprises 2 A sequence. In certain embodiments, the polynucleotide sequence may encodes multiple polypeptides. The sequences encoding the multiple polypeptides may be polycistronic, connected by 2 A or IRES sequences. In certain embodiments, the polynucleotide sequence comprises a signal-peptide encoding sequence at its 5' end.

In certain embodiments, the double-strand break is generated via introducing into the cell a composition comprising a site-specific nuclease. In certain embodiments, site-specific nuclease is a CRISPR-associated (Cas) nuclease, a transcription activator-like effector nuclease (TALEN), or a zinc finger nuclease (ZFN). In certain embodiments, the composition further comprises a CRISPR-Cas guide RNA directed to the target location. In certain embodiments, the site-specific nuclease is a zinc finger nuclease (ZFN), or a TALE-nuclease (TALEN). In the CRISPR/Cas system, the double-strand break is generated by the CRISPR nuclease oriented by the Cas guide RNA that is designed according to the sequence at the target location.

In certain embodiments, the target location can be any locus of a genome, including coding and non-coding region and safe harbor locus, such as e.g. Hipp11 (H11) locus, ROSA26 locus, Rosa26 like locus (LLC), HPRT, or AAVS1. In certain embodiments, the cell is a eukaryotic cell, e.g., a mammalian or human cell. In certain embodiments the cell is in vitro, ex vivo or in vivo. In certain embodiments, the cell is a one-cell embryo.

BRIEF DESCRIPTION OF THE FIGURES

FIG. 4A shows the schematic of fused mouse Alb mRNA with BDD-F8 transgene integration between Alb exon 13 and exon 14. Arrow sets indicated the primers used for RT-PCR and sequencing analyses. FIG. 4B shows RT-PCR analyses using the primers as indicated. Each lane represented one individual mouse liver RNA sample. Of note, in both mice received $2\times10^{13}$ gc/kg AAV8 virus, a knock-in event of BDD-F8 transgene to the Alb locus was seen in liver cells, as judged by two independent PCR products with the expected molecular weight (393 bp by primers ex13-F1 and BDD-F8-R1, and 171 bp by primers ex13-F2 and BDD-F8-R2).

FIG. 6A shows the tail bleeding during the first 30 min in hemophilia mice injected with escalating virus dosages, sampled every 4 min. FIG. 6B shows the total blood loss within the first 30 min. Results were shown in *P<0.05, P<0.01 vs. F8 KO with vehicle, #P>0.2 vs. WT with vehicle, n=3-5 mice per group. FIG. 6**C shows the average end-point bleeding speed within the first 30 min. Results were shown in *P<0.05, **P<0.01 vs. F8 KO with vehicle, #P>0.3 vs. WT with vehicle, n=3-5 mice per group.

DESCRIPTION OF THE INVENTION

Figure 1:
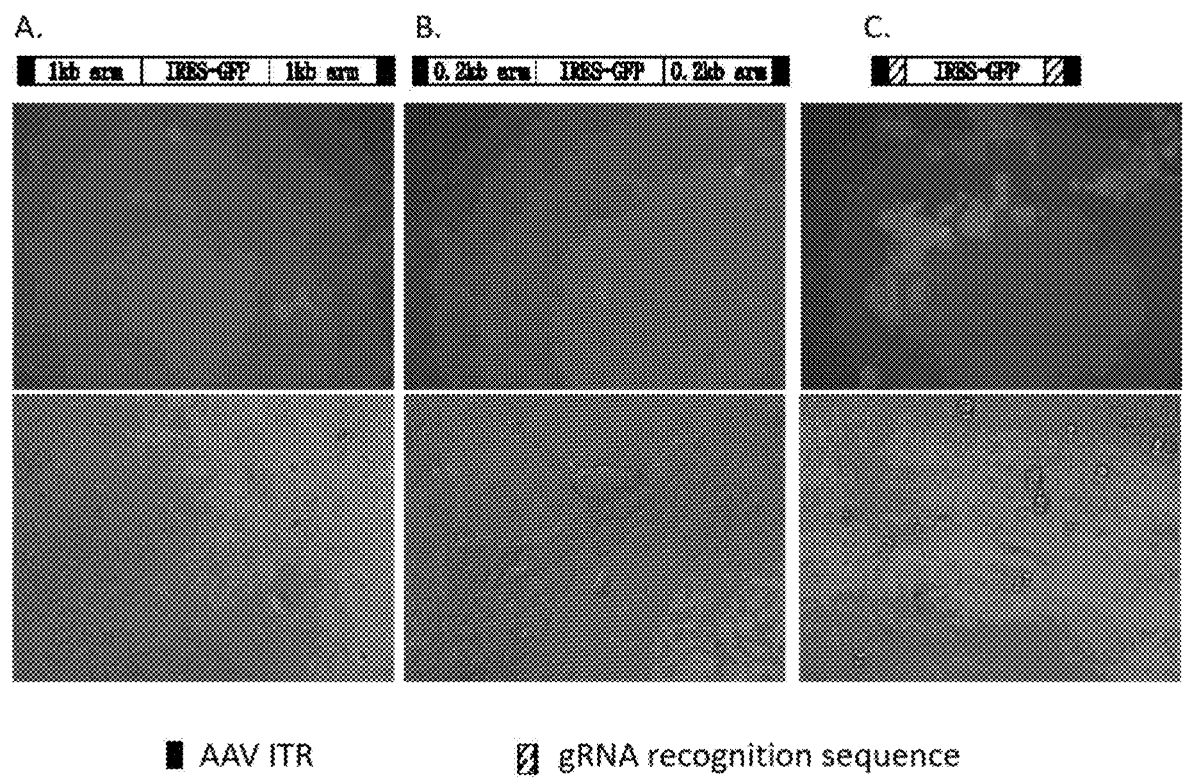
FIGS. 1A-1C show the GFP signal of the HEK293 cells infected with a AAV expressing Cas9 and a gRNA targeting the 3' end of GAPDH gene together with a donor AAV virus that includes: (1) The IRES-GFP with an 1 kb homologous arm at each end (FIG. 1A); (2) The IRES-GFP with a 0.2 kb homologous arm at each end (FIG. 1B); (3) The IRES-GFP with no arm, instead with a gRNA targeting sequence, at each end (FIG. 1C). Schemes for the donor virus constructions are shown at the top panel. The GFP signal images are shown in the middle panel, and the bright field images at the bottom panel.

We have developed methods and compositions of inserting a polynucleotide sequence into a genome of a cell. In one aspect, the method comprises generating a double-strand break at a target site of the genome and introducing into the cell a virus. The virus comprises a nucleic acid comprising the polynucleotide sequence to be inserted or the complementary sequence thereof. The nucleic acid does not comprise a homologous arm corresponding to the target site. In certain embodiments, the nucleic acid comprises a very short (5~25 bp) microhomologous arms corresponding to the target site. In another aspect, a composition for inserting a polynucleotide sequence into a genome of a cell is provided. The composition comprises a site-specific nuclease capable of generating a DNA double-strand break at a target site of the genome and a virus comprising a nucleic acid comprising the polynucleotide sequence or the complementary sequence thereof.

Definition

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the term "homologous arm" refers to a DNA sequence on a gene-targeting vector that facilitates the recombination between the vector and the target genome. Typically, the gene-targeting vector comprises two homologous arms flanking the gene of interest (i.e., gene to be inserted to the target genome). The two homologous arms have DNA sequences are identical to the target genome. As used herein, the homologous arm has a length of at least 50 bp, typically at least 500 bp in length. For the purposes of clarity, as used herein, DNA sequences identical to the target genome but very short in length (5-25 bp) are called "microhomologous arm," which is not "homologous arm" as defined in this disclosure.

The term "introduce" in the context of inserting a nucleic acid sequence into a cell, means "transfection", or "transformation," or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon. The vector of the present disclosure may be introduced into a cell using any method known in the art. Various techniques for transforming animal cells may be employed, including, for example: microinjection, retrovirus mediated gene transfer, electroporation, transfection, or the like (see, e.g., Keown et al., Methods in Enzymology 1990, 185:527-537). In one embodiment, the vector is introduced to the cell via a virus.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

As used herein, a "promoter" is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

The term "nucleic acid" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "double-stranded" as used herein refers to one or two nucleic acid strands that have hybridized along at least a portion of their lengths. In certain embodiments, "double-stranded" does not mean that a nucleic acid must be entirely double-stranded. Instead, a double-stranded nucleic acid can have one or more single-stranded segment and one or more double-stranded segment. For example, a double-strand nucleic acid can be a double-strand DNA, a double-strand RNA, or a double-strand DNA/RNA compound. The form of the nucleic acid can be determined using common methods in the art, such as molecular band stained with sybergreen and distinguished by electrophoresis, In general, a "protein" is a polypeptide {i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

As used herein, the term "locus" is the specific physical location of a DNA sequence (e.g. of a gene) on a chromosome. The term "safe harbor locus" refers to a locus within the genome allowing safe expression of a transgene through targeted insertion. The safe harbor locus may either be located within the intron of a gene, or within an intergenic region. Ideally, insertion into a safe harbor locus should have no impact on, or not substantially modify the expression of other genes located in the vicinity of the target sequence, or insertion of a genetic element into said locus does preferably not substantially modify the phenotype of said cell, tissue or individual (except for the phenotype due to expression of the genetic element). Examples of the safe harbor locus are Hipp11 (H11) locus, ROSA26 locus, Rosa26 like locus (LLC), HPRT, AAVS1, or CCR5 or multiple antibiotic resistance (mar) locus.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%>, 70%>, 80%>, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

Viruses and Packaging Cells

A virus as used herein refers to a genetically modified viral vector comprising a gene fragment of interest. In certain embodiments, the viruses are rendered replication deficient through genetic manipulation so that there will be no progeny virus produced after primary infection. Some or most of the viral gene encoding viral proteins that are essential for virus replication are removed, except for the viral nucleic acid sequences that are critical for viral genome replication and packaging. These replication incompetent viral vectors are usually 1) produced from packaging cell lines that provide all the viral proteins that are essential to complement replication of viral vectors or 2) produced with helper viruses in the case of AAV vector. Viruses that have been developed for gene transduction are grouped as those of integrating into the host cell genome and those of non-integrating vectors. In certain embodiments, the viruses used herein integrate into the host cell genome. In other embodiments, the viruses used herein do not integrate into the host cell genome. In some embodiments, the virus causes transient expression of the gene of interest and/or the guide RNA (i.e. gRNA) molecule. In other embodiments, the virus causes long-lasting, e.g., at least 1 week, 2 weeks, 1 month, 2 months, 3 months, 6 months, 9 months, 1 year, 2 years, or permanent expression, of the gene of interest and/or the gRNA molecule. In some embodiments, the virus is engineered to have reduced immunity, e.g., in an animal.

The use of DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (in vivo). Conventional viral based systems (e.g. dsDNA or ssDNA virus) could include retrovirus, lentivirus, adenovirus, adeno-associated virus (AAV), vaccinia viruses, poxvirus and herpes simplex virus or vectors thereof for gene transfer. In some embodiments, the virus infects dividing cells. In other embodiments, the virus infects non-dividing cells. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

In certain embodiments, the packaging capacity of the viruses is at least, e.g., about 2 kb, about 3 kb, about 4 kb, about 5 kb, about 10 kb, about 15 kb, about 20 kb, about 25 kb, about 30 kb, about 35 kb, about 40 kb, about 45 kb, about 50 kb, about 60 kb, about 70 kb, about 80 kb, about 90 kb, or about 100 kb.

In certain embodiments, the virus/viral vector used herein is an AAV capsid comprising a capsid sequence of the serotype AAV1, AAV2, AAV3, AAV4, AAV5, AAV6, AAV7, AAV8, AAV9, AAV.rh8, AAV.rh10, AAV.rh32/33, AAV.rh43, AAV.rh64R1, or AAV7m8, or a capsid sequence that are at least 50%, at least 60%, at least 70%, at least 80%, at least 90%, or at least 95% or greater identical to the capsid sequence of the above serotypes. In certain embodiments, the virus/viral vector used herein is a chimeric AAV capsid including AAV9i1, AAV2i8, AAV-DJ, AAV2G9, AAV2i8G9, or AAV8G9.

In certain embodiments, the AAV is a self-complementary adeno-associated virus (scAAV), e.g., a scAAV that packages both strands which anneal together to form dsDNA. In certain embodiments, the gene of interest is delivered by a hybrid virus of one or more of the viruses mentioned in the present disclosure, for example, a hybrid of an AAV (e.g. of any AAV serotype) with a Bocavirus, B19 virus, porcine AAV, goose AAV, feline AAV, canine AAV, or MVM.

In certain embodiment, the virus/viral vector recognizes a specific cell type, organ or tissue. For example, the virus/viral vector can be pseudotyped with an alternative/different viral envelope glycoprotein; engineered with a cell type-specific receptor (e.g., genetic modification(s) of one or more viral envelope glycoproteins to incorporate a targeting ligand such as a peptide ligand, a single chain antibody, or a growth factor); and/or engineered to have a molecular bridge with dual specificities with one end recognizing a viral glycoprotein and the other end recognizing a moiety of the target cell surface (e.g., a ligand-receptor, monoclonal antibody, avidin-biotin and chemical conjugation).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely Rep and Cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

Virus/viral vectors that integrate are mainly made from retroviruses such as murine leukemia virus (MuLV) and lentiviruses (HIV-1, SIV, FIV, and BIV). These retroviral vectors can introduce and permanently integrate nucleic acids into host genomes. The non-integrating vectors can be vectors developed from DNA viruses such as adenovirus, adeno-associated virus (AAV), herpes simplex virus (HSV), papovavirus (e.g. simian virus 40 (SV40)), and poxviruses (vaccinia virus). Both adenoviral vector and AAV vector are widely used non-integrating vectors.

In certain embodiments, the virus comprises a non-viral, or heterologous sequence to be expressed or delivered by a virus of the disclosure. Non-limiting examples of non-viral, or heterologous sequences include cDNAs, shRNAs, miRNAs, ribozymes, and antisense sequences. For example, the Cas9- and/or gRNA-encoding DNA can be delivered by a non-vector based system (e.g., using naked DNA or DNA complexes). In certain embodiments, the DNA can be delivered, e.g., by organically modified silica or silicate (Ormosil), electroporation, transient cell compression or squeezing (see, e.g., Lee 2012), gene gun, sonoporation, magnetofection, lipid-mediated transfection, dendrimers, inorganic nanoparticles, calcium phosphates, or a combination thereof.

In certain embodiments, the DNA in the CRISPR/Cas9 system is delivered by a combination of a vector and a non-vector based method. For example, the nucleic acid for the Cas9 comprises a sequence encoding a gRNA molecule comprising a targeting domain that is complementary to a target DNA sequence in the target gene, and the nucleic acid for the gRNA comprises a sequence encoding a Cas9 molecule. In another embodiment, the CRISPR/Cas9 system may further comprises a sequence that encodes a second, third and/or fourth gRNA molecule as described herein. In certain embodiment, each gRNA sequence may be present on the same nucleic acid molecule, e.g., the same vector, e.g., the same virus/viral vector, e.g., the same adeno-associated virus (AAV) vector. In certain embodiments, the nucleic acid molecule is an AAV vector. In certain embodiments, each gRNA sequence is present on different nucleic acid molecules, e.g., different vectors, e.g., different viral vectors, e.g., different adeno-associated virus (AAV) vectors. In certain embodiments, the sequences encoding the gRNA molecules may be operably linked to a promoter, or to different promoters.

In certain embodiment, the Cas9 sequence and the gRNA sequences are present on the same nucleic acid molecule, e.g., the same vector, e.g., the same viral vector, e.g., the same adeno-associated virus (AAV) vector. In certain embodiments, the Cas9 sequence and the gRNA sequences are present on different nucleic acid molecules, e.g., different vectors, e.g., different viral vectors, e.g., different adeno-associated virus (AAV) vectors. In certain embodiments, the sequences encoding the Cas9 molecules may be operably linked to the same promoter as of the gRNA sequences, or to a different promoter than that of the gRNA sequences. In certain embodiment, the nucleases are delivered as protein or ribonucleoprotein (RNP) with gRNA.

A cell can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ (e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell); a cell from an endocrine system or organ (e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte)); a cell from a nervous system or organ (e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph)); a cell from a respiratory system or organ (e.g., a pneumocyte (a type I pneumocyte and a type II pneumocyte), a clara cell, a goblet cell, an alveolar macrophage); a cell from circular system or organ (e.g., myocardiocyte and pericyte); a cell from digestive system or organ (e.g., a gastric chief cell, a parietal cell, a goblet cell, a paneth cell, a G cell, a D cell, an ECL cell, an I cell, a K cell, a S cell, an enteroendocrine cell, an enterochromaffin cell, an APUD cell, a liver cell (e.g., a hepatocyte and Kupffer cell)); a cell from integumentary system or organ (e.g., a bone cell (e.g., an osteoblast, an osteocyte, and an osteoclast), a tooth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell)), a muscle cell (e.g., myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula densa cell), and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell).

A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A stem cell can be hematopoietic stem and progenitor cell (HSPC), or mesenchymal stem cell, or multipotent stromal cell (MSC).

A mammalian cell can be a rodent cell, e.g., a mouse, rat, hamster cell. A mammalian cell can be a lagomorpha cell, e.g., a rabbit cell. A mammalian cell can also be a primate cell, e.g., a human cell. In certain examples, the cells are those used for protein bioproduction, e.g., CHO cells.

As used herein, a cell can be isolated (e.g., in vitro cultured) or not isolated (e.g., in a tissue or organism). In certain embodiments, a virus is delivered to cells in vivo.

Site-Specific Cleavage System

As used herein, a "nuclease" is an enzyme capable of cleaving the phosphodiester bonds between the nucleotide subunits of nucleic acids. A "nuclease domain" is an independently folded protein domain having nuclease activity. A "site-specific nuclease" refers to a nuclease whose functioning depends on a specific nucleotide sequence. Typically, a site-specific nuclease recognizes and binds to a specific nucleotide sequence and cuts a phosphodiester bond within the nucleotide sequence. In certain embodiments, the double-strand break is generated by site-specific cleavage using a site-specific nuclease. Examples of site-specific nucleases include, without limitation, zinc finger nucleases (ZFNs), transcriptional activator-like effector nucleases (TALENs) and CRISPR (clustered regularly interspaced short palindromic repeats)-associated (Cas) nucleases.

A site-specific nuclease typically contains a DNA-binding domain and a DNA-cleavage domain. For example, a ZFN contains a DNA binding domain that typically contains between three and six individual zinc finger repeats and a nuclease domain that consists of the FokI restriction enzyme that is responsible for the cleavage of DNA. The DNA binding domain of ZFN can recognize between 9 and 18 base pairs. In the example of a TALEN, which contains a TALE domain and a DNA cleavage domain, the TALE domain contains a repeated highly conserved 33-34 amino acid sequence with the exception of the $12^{th}$ and $13^{th}$ amino acids, whose variation shows a strong correlation with specific nucleotide recognition. For another example, Cas9, a typical Cas nuclease, is composed of an N-terminal recognition domain and two endonuclease domains (RuvC domain and HNH domain) at the C-terminus.

In certain embodiments, the site-specific nuclease is a Cas protein. In such case, the composition may also contain a CRISPR-Cas guide RNA directed to the target DNA sequence to form a CRISPR complex at the target DNA sequence. A CRISPR complex is formed in junction with a Cas protein, a guide RNA, a target sequence with PAM, and a tracr RNA (which can be fused with the guide RNA or separated from the guide RNA).

As used herein, a "Cas protein" refers to a polypeptide that binds to the guide RNA and exhibit nuclease activity. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. These enzymes are known; for example, the amino acid sequence of *S. pyogenes* Cas9 protein may be found in the SwissProt database under accession number Q99ZW2. In some embodiments, the unmodified Cas protein has DNA cleavage activity. In some embodiments, the Cas protein directs cleavage of one or both strands at the location of a target sequence, such as within the target sequence and/or within the complement of the target sequence. In some embodiments, the Cas protein directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, the Cas protein is mutated such that the mutated Cas protein lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A.

As used herein, a "CRISPR-Cas guide RNA" or "guide RNA" or "gRNA" refers to an RNA that directs sequence-specific binding of a CRISPR complex to the target sequence. Typically, a guide RNA comprises (i) a guide sequence that has sufficient complementarity with a target polynucleotide sequence to hybridize with the target sequence and (ii) a trans-activating cr (tracr) mate sequence. A guide RNA may further comprises a tracr RNA fused at the 3' end, resulting a single chimeric guide RNA. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and P A Carr and G M Church, 2009, *Nature Biotechnology* 27(12): 1151-62).

As used herein, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher.

In some embodiments, the guide RNA or gRNA comprises a guide sequence fused to a tracr sequence, i.e., the tracr sequence and tracr mate sequence are contained within a single transcript, such that hybridization between the two produces a transcript having a secondary structure, such as a hairpin. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. Preferred loop-forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the present application, the guide RNA has at least two or more hairpins. In preferred embodiments, the guide RNA has two, three, four or five hairpins. In a further embodiment of the invention, the guide RNA has at most five hairpins. In some embodiments, the guide RNA further includes a transcription termination sequence, preferably a polyT sequence, for example six T nucleotides. In some embodiments, the tracr sequence is a separate transcript from a transcript comprising the tracr mate sequence. In certain embodiments, tracr sequence is in a separate vector from the guide RNA (see, e.g., US PG Pub No. 20140068797).

As used herein, the term Protospacer adjacent motif (PAM) refers to a DNA sequence immediately following the DNA sequence targeted by Cas protein. In some embodiments, PAM sequence is located at the 3' end of the target sequence and is required for the Cas protein to successfully bind to the target sequence. The PAM sequence varies by the species of the bacteria from which the Cas protein is derived. For example, the PAM sequence for Cas9 from *Steptococcus pyogenes* is NGG (N could be any of A, T, C or G). For another example, the PAM sequence for *Neisseria meningitides* is NNNNGATT. The PAM sequence for *Streptococcus thermophiles* is NNAGGAA. The PAM sequence for *Treponema denticola* is NAAAAC.

Cas molecules can be delivered into cells by any method known in the art. For example, Cas protein molecules can be delivered, e.g., by microinjection, electroporation, transient cell compression or squeezing (see, e.g., Lee 2012), lipid-mediated transfection, peptide-mediated delivery, nanoparticle delivery, or a combination thereof. In certain embodiments, the delivery is accompanied by DNA encoding a gRNA (or DNAs encoding the gRNAs) or by a gRNA (or gRNAs). In certain embodiments, Cas protein is conjugated to molecules promoting uptake by the target cells. In certain embodiments, Cas protein forms a ribonucleoprotein (RNP) with gRNA and delivered into the target cells.

In certain embodiments, the sequence-specific nuclease domain is a zinc finger nuclease (ZFN). Zinc finger nucleases are artificial restriction enzymes generated by fusing a zinc finger DNA-binding domain to a DNA-cleavage domain. Zinc finger domain can be engineered to target specific desired DNA sequences, which directs the zinc finger nucleases to cleave the target DNA sequences.

Typically, a zinc finger DNA-binding domain contains three to six individual zinc finger repeats and can recognize between 9 and 18 base pairs. Each zinc finger repeat typically includes approximately 30 amino acids and comprises a ββα-fold stabilized by a zinc ion. Adjacent zinc finger repeats arranged in tandem are joined together by linker sequences.

Various strategies have been developed to engineer zinc finger domains to bind desired sequences, including both "modular assembly" and selection strategies that employ either phage display or cellular selection systems (Pabo C O et al., "Design and Selection of Novel Cys2His2 Zinc Finger Proteins" Annu. Rev. Biochem. (2001) 70: 313-40). The most straightforward method to generate new zinc-finger DNA-binding domains is to combine smaller zinc-finger repeats of known specificity. The most common modular assembly process involves combining three separate zinc finger repeats that can each recognize a 3 base pair DNA sequence to generate a 3-finger array that can recognize a 9 base pair target site. Other procedures can utilize either 1-finger or 2-finger modules to generate zinc-finger arrays with six or more individual zinc finger repeats. Alternatively, selection methods have been used to generate zinc-finger DNA-binding domains capable of targeting desired sequences. Initial selection efforts utilized phage display to select proteins that bound a given DNA target from a large pool of partially randomized zinc-finger domains. More recent efforts have utilized yeast one-hybrid systems, bacterial one-hybrid and two-hybrid systems, and mammalian cells. A promising new method to select novel zinc-finger arrays utilizes a bacterial two-hybrid system that combines pre-selected pools of individual zinc finger repeats that were each selected to bind a given triplet and then utilizes a second round of selection to obtain 3-finger repeats capable of binding a desired 9-bp sequence (Maeder M L, et al., "Rapid 'open-source' engineering of customized zinc-finger nucleases for highly efficient gene modification". Mol. Cell. (2008) 31 (2): 294-301).

The non-specific cleavage domain from the type II restriction endonuclease FokI is typically used as the cleavage domain in ZFNs. This cleavage domain must dimerize in order to cleave DNA and thus a pair of ZFNs are required to target non-palindromic DNA sites. Standard ZFNs fuse the cleavage domain to the C-terminus of each zinc finger domain. In order to allow the two cleavage domains to dimerize and cleave DNA, the two individual ZFNs must bind opposite strands of DNA with their C-termini a certain distance apart. The most commonly used linker sequences between the zinc finger domain and the cleavage domain requires the 5' edge of each binding site to be separated by 5 to 7 bp.

In certain embodiments, the sequence-specific nuclease domain is a transcription activator-like effector nuclease (TALEN). TALEN are artificial restriction enzymes made by fusing a transcription activator-like effector (TALE) DNA-binding domain to a DNA cleavage domain (e.g., a nuclease domain), which can be engineered to cut specific sequences. TALEs are proteins that are secreted by *Xanthomonas* bacteria via their type III secretion system when they infect plants. TALE DNA-binding domain contains a repeated highly conserved 33-34 amino acid sequence with divergent $12^{th}$ and $13^{th}$ amino acids, which are highly variable and show a strong correlation with specific nucleotide recognition. The relationship between amino acid sequence and DNA recognition allows for the engineering of specific DNA-binding domains by selecting a combination of repeat segments containing the appropriate variable amino acids. The non-specific DNA cleavage domain from the end of the FokI endonuclease can be used to construct TALEN. The FokI domain functions as a dimer, requiring two constructs with unique DNA binding domains for sites in the target gemone with proper orientation and spacing. See Boch, Jens "TALEs of genome targeting". Nature Biotechnology. (2011) 29 (2): 135-6; Boch, Jens et al., "Breaking the Code of DNA Binding Specificity of TAL-Type III Effectors" Science (2009) 326 (5959): 1509-12; Moscou M J and Bogdanove A J "A Simple Cipher Governs DNA Recognition by TAL Effectors" Science (2009) 326 (5959): 1501; Juillerat A et al., "Optimized tuning of TALEN specificity using non-conventional RVDs" Scientific Reports (2015) 5: 8150; Christian et al., "Targeting DNA Double-Strand Breaks with TAL Effector Nucleases" Genetics (2010) 186 (2): 757-61; Li et al., "TAL nucleases (TALNs): hybrid proteins composed of TAL effectors and FokI DNA-cleavage domain" Nucleic Acids Research (2010) 39: 1-14.

As used herein, a "target DNA sequence" refers to a sequence recognized by the site-specific nuclease domain. In some embodiments, the target DNA sequence is a sequence within a genome of a cell. Exemplary target sequences include those that are unique in the target genome. In some embodiments, a target DNA sequence is located in the nucleus or cytoplasm of a cell. In some embodiments, the target sequence may be within an organelle of a eukaryotic cell, for example, mitochondrion or chloroplast.

In certain embodiments that the site-specific nuclease domain is a Cas protein, a target sequence refers to a sequence to which a guide sequence is designed to have complementarity, where hybridization between a target sequence and a guide sequence promotes the formation of a CRISPR complex. The components of a CRISPR complex and the mechanism of using a CRISPR complex for gene editing has been described (e.g., M Jinek et al., Science, 2012, 337: 816-821; L Cong et al., Science, 2012, 339:819-823; PCT Publication WO2013176772, WO2013169802, WO2014018423 and U.S. Pat. No. 8,697,359). A target sequence can be any sequence in the genome of a target cell so long as the target sequence comprises a Protospacer Adjacent Motif (PAM) sequence, which is required by the formation of a CRISPR complex at the target sequence, at the 3' end of the target sequence. Exemplary target sequences include those that are unique in the genome of a target cell. For example, for the *S. pyogenes* Cas9, a unique target sequence in a genome may include a Cas9 target site of the form MMMMMMMMNNNNNNNNNNNNXGG where NNNNNNNNNNNNXGG (N is A, G, T, or C; and X can be any nucleotide) has a single occurrence in the genome. In this case, NNNNNNNNNNNN is complementary to a guide RNA and XGG is a PAM sequence. For the *S. Thermophiles* CRISPR1Cas9, a unique target sequence in a genome may include a Cas9 target site of the form MMMMMMMMNNNNNNNNNNNNXXAGAAW (SEQ ID NO: 6) where NNNNNNNNNNNNXXAGAAW (SEQ ID NO: 7, N is A, G, T, or C; X can be any nucleotide; and W is A or T) has a single occurrence in the genome. In each of these sequences "M" may be A, G, T, or C, and need not be considered in identifying a sequence as unique.

Donor Virus and Gene Editing Techniques

In certain embodiments, the virus is used as a donor for gene delivery in gene knock-in (KI) step after generation of the double-strand break. The double-strand break (DSB) created by the CRISPR complex can be repaired by a repair processes such as the non-homologous end joining (NHEJ) pathway or the homology-directed repair (HDR) (see Moore J K, Haber J E, 1996. "Cell cycle and genetic requirements of two pathways of nonhomologous end-joining repair of double-strand breaks in *Saccharomyces cerevisiae*". 16 (5): 2164-73). While HDR refers to the process of repairing DNA damage using a homologous nucleic acid (e.g., an endogenous homologous sequence, e.g., a sister chromatid, or an exogenous nucleic acid, e.g., a template nucleic acid), there are two types of HDR, canonical HDR and alternative HDR. Typically, canonical HDR functions when there has been significant resection at the double-strand break, forming at least one single stranded portion of DNA. Alternative HDR (i.e. Alt-HDR) refers to the process of repairing DNA damage using a homologous nucleic acid (e.g., an endogenous homologous sequence, e.g., a sister chromatid, or an exogenous nucleic acid, e.g., a template nucleic acid). Alt-HDR differs from canonical HDR in that the process utilizes different pathways from canonical HDR, and can be inhibited by the canonical HDR mediators, RAD51 and BRCA2. Alt-HDR uses a single-stranded or nicked homologous nucleic acid for repair of the break.

NHEJ often results in inserts/deletions (InDels) at the DSB site. NHEJ is "non-homologous" because the break ends are directly ligated without the need for a homologous template, in contrast to homology directed repair (HDR), which requires a homologous sequence to guide repair. NHEJ is an evolutionarily conserved system throughout all kingdoms of life and is the predominant double-strand break repair pathway in mammalian cells. NHEJ can also be classified as canonical NHEJ and alternative NHEJ. Unless specified, the term "NHEJ" as used herein encompasses canonical NHEJ and alternative NHEJ.

Canonical NHEJ refers to the process of repairing double-strand breaks in which the break ends are directly ligated and requires the Ku heterodimer (Ku70/Ku80), the catalytic subunit of DNA-PK (DN-PKcs), and/or DNA ligase XRCC4/LIG4.

In certain embodiments, the DSB are repaired by canonical NHEJ in more than 10%, 20%, 30%, 40%, 50%, 60%, 70%, 80%, 90%, 95% or more in the population of cells.

In alternative NHEJ (Alt-NHEJ), a small degree of resection occurs at the break ends on both sides of the break to reveal single-stranded overhangs. Ligation or annealing of the overhangs results in the deletion of sequence. Examples of pathways that are categorized as alternative NHEJ include blunt end-joining (blunt EJ) and microhomology mediated end joining (MMEJ) leading to deletions, as well as synthesis dependent microhomology mediated end joining (SD-MMEJ), leading to the formation of insertions (see Ottaviani Diego et al., The role of microhomology in genomic structural variation, Trends in Genetics, Vol 30, Issue 3, 2014, Pages 85-94). In certain embodiments, the alternative NHEJ results in an insertion in the target gene. Typically, Alt-NHEJ utilizes short homologous DNA sequences (microhomologies) to guide repair, while these microhomologies are often present in single-stranded overhangs on the ends of double-strand breaks. When the overhangs are perfectly compatible, Alt-NHEJ usually repairs the break accurately. In certain embodiments, the CRISPR-created site-specific DSB with short DNA sequences homologous to the target site can form a 5' overhang and a 3' overhang.

In certain embodiments, the 5' overhang and 3' overhang in the DSB are repaired by Alt-NHEJ in more than 10%, 20%, 30%, 40%, 50%, 60%, 70%, 80%, 90%, 95% or more in the population of cells.

In the present disclosure, the target DNA sequence is cut by the CRISPR complex and a gene of interest is inserted to the site of break. The gene of interest is delivered by a donor virus, such as an AAV virus.

The donor virus/viral vector carrying the gene of interest comprising a polynucleotide sequence encodes proteins include, but not limited to, proteins selected from the group consisting of: alpha-1 antitrypsin, angiostatin, antihemolytic factor, antibody, antibody fragments, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-I beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor 1, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

In certain embodiment, the gRNA sequence can be present on the same nucleic acid molecule of the donor virus/viral vector, e.g., the same vector, e.g., the same virus/viral vector, e.g., the same adeno-associated virus (AAV) vector. In certain embodiments, the nucleic acid molecule is an AAV vector. In certain embodiments, the gRNA sequence is present on different nucleic acid molecules from the donor virus/viral vector, e.g., different vectors, e.g., different viral vectors, e.g., different adeno-associated virus (AAV) vectors.

In certain embodiments, the methods disclosed herein use AAV to deliver a gene of interest and insert such a gene sequence through NHEJ pathway. Whereas AAV packages a single strand of DNA and its second strand is synthesized after AAV gets into the cell. The methods disclosed take advantage of this dsDNA intermediate of AAV to insert transgene through the NHEJ pathway. The combination of AAV donor and NHEJ not only maximizes the size of the transgene to be inserted due to no need of homologous arms, but also increases the efficiency of gene editing over HDR. A skilled artisan will appreciate that the NHEJ method does not limit only to AAV, but it can be applied to other dsDNA viruses including viruses going through dsDNA intermediates.

Advantages of the NHEJ method combining with the viruses embody in various potential applications in, for example, gene editing at an optional locus of the genome, including coding and non-coding regions, as well as safe harbor locus, without bothering the homologous arms that limit the packaging size of the gene of interest, thereby greatly broaden the applicability of cell and animal gene modifications, and gene and cell therapies. Same principle applies to the donors with short homologous arms, which also increase packaging size of the gene of interest, and can be used for alternative NHEJ, such as MMEJ, for gene editing.

EXAMPLES

Example 1: Comparison of Knock-in Efficiency with AAV HDR Donors and a NHEJ Donor HEK293 cells were infected with a Cas9 and gRNA virus targeting the 3'UTR region of GAPDH gene and a donor virus. The cells with on target knock-in give a green GFP signal. Three donor viruses are generated as below: (1) IRES-GFP with a 1 kb arm homologous to the target site at each end; (2) IRES-GFP with a 0.2 kb arm at each end; (3) IRES-GFP with no arm, instead with a gRNA targeting sequence, at each end. The viral constructs are shown in FIG. 1.

As shown in FIG. 1, the HEK293 cells infected with (1) or (2) showed low GFP signal. In contrast, the HEK293 cells infected with construct (3) showed higher GFP signal.

Figure 2:
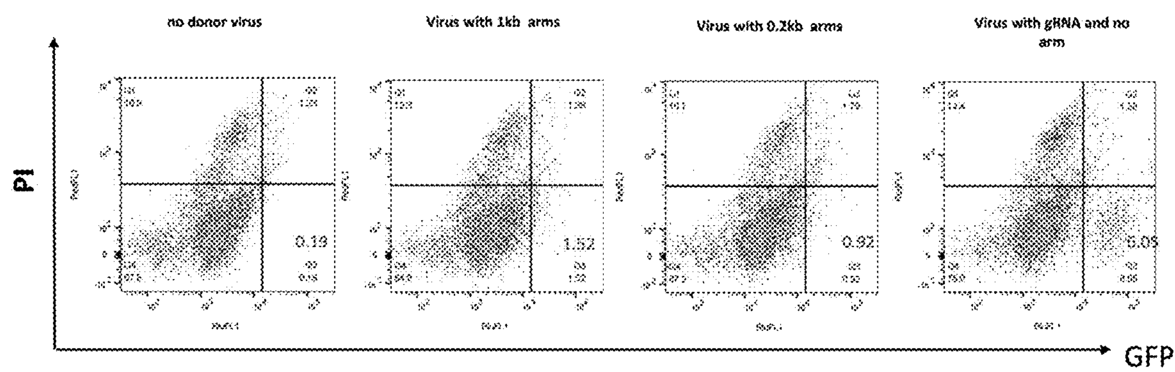
FIG. 2 illustrates the above treated HEK293 cells as measured by FACS. Y axis: Intensity of PI staining. X axis: Intensity of GFP signal.

FIG. 2 shows the cells infected with the viruses as measured by FACS, indicating that cells infected with viruses carrying NHEJ donor has higher knock-in efficiency than viruses carrying HDR donor.

Example 2: B Domain Deleted Factor VIII (BDD F8) Knock-in (KI) at ALB Locus Through NHEJ Coagulation factor VIII or "FVIII" is a blood-clotting protein that has a GenBank Reference ID NP_000123 (preproprotein) or NP_063916. FVIII is an essential component in the coagulation cascade. It is a cofactor for Factor IXa that, in the presence of $Ca^{2+}$ and phospholipids forms a complex that converts Factor X to the activated form Xa. FVIII circulates in the bloodstream in an inactive form, bound to von Willebrand factor. In the event of an injury that damages blood vessels, FVIII is activated and separated from von Willebrand factor. The active FVIII or FVIIIa interacts with FIX to trigger a chain reaction that form a blood clot. Full length F8 gene coding sequence is over 7 kb, which is beyond the 4.7 kb package size of AAV.

Figure 3:
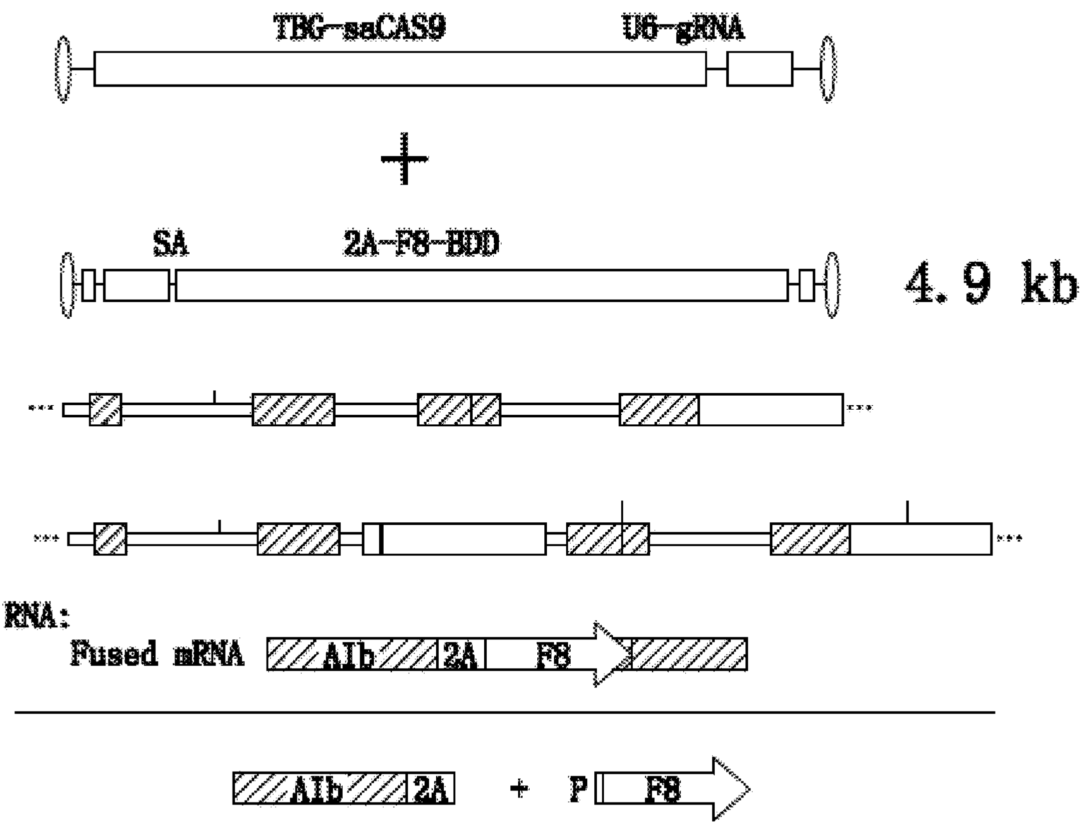
FIG. 3 illustrates the scheme for knock-in the BDD F8 at ALB locus via NHEJ using an AAV expressing Cas9 from *Staphylococcus aureus* (SaCas9) nuclease and gRNA (SEQ ID NO:5) and a donor AAV virus without homologues arms. The gRNA targeting site was in the intron upstream of the last coding exon of human albumin gene. The donor vector encodes a BDD F8 preceded by a 2 A-peptide coding sequence, a coding sequence of the 13 amino acids of the last coding exon and a transcription splicing signal (SA). Two gRNA recognition sequences that flank the insertion sequence were cloned into the vector. Upon co-infection of the Cas9/gRNA and the donor viruses, Cas9/gRNA will target the genomic site and cleave the double-stranded donor virus intermediate. The linearized donor DNA will be inserted to the genomic site through NHEJ. Half of the integration will lead to ALB and BDD-F8 fusion at the DNA and RNA levels, but as the result of ribosomal skipping during translation, ALB and BDD-F8 are produced as two separate proteins.

B-domain deleted factor VIII (BDD FVIII) (SEQ ID NO: 1) is a deletion form of coagulation factor VIII. Recombinant BDD FVIII in functional in vitro and in vivo. BDD F8 gene (SEQ ID NO: 2) is a 4.4 kb fragment. With homologous arms and/or promoters and other expression elements, it will be difficult for AAV packaging. Elimination of homologous arms makes it small enough for virus packaging (see FIG. 3).

In order to identify the gene insertion of BDD F8, F8 knock-out (KO) male mice were injected via tail vein with AAV8-SaCas9-gRNA1 (SEQ ID NO: 3) and AAV8-BDD-F8 (SEQ ID NO: 4) donor viruses at a ratio of 1:8 with a total viral dosage of $2\times10^{13}$, $2\times10^{12}$, or $2\times10^{11}$ gc (genome copy)/kg, respectively. Four weeks after injection, liver tissues were harvested and total RNA was purified and was subjected to RT-PCR and sequencing analysis.

Figure 4A:
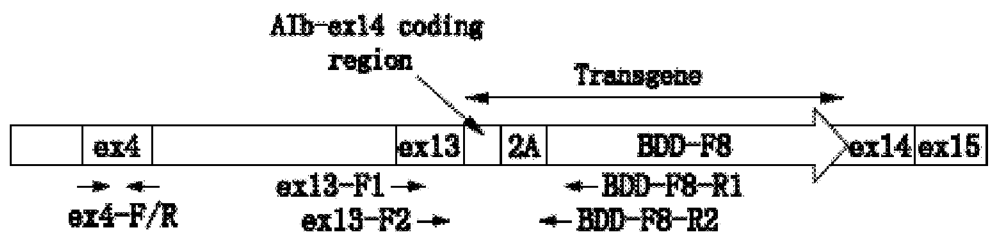
FIGS. 4A-4B represent the RT-PCR and sequencing analyses of BDD-F8 transgene knock-in at the Alb locus in mouse liver cells.
Figure 4B:
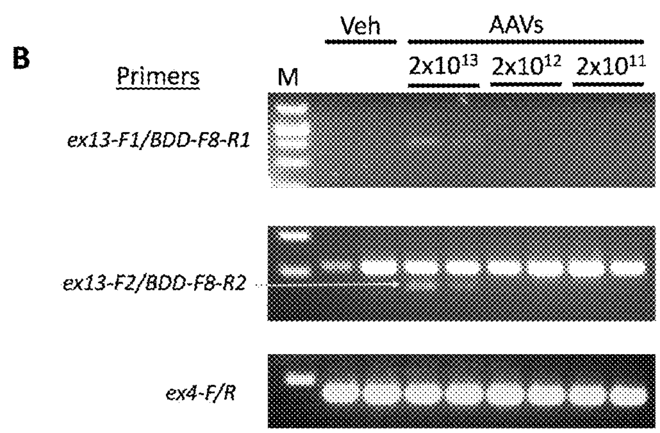

The RT-PCR result and sequencing of BDD-F8 transgene knock-in at the Alb locus were shown in FIG. 4B, which indicates that the BDD F8 has been successfully inserted into the intended location of the mouse genome.

Example 3: Effects of F8 Knock-in in Hemophilia Mouse Model

The effects of the BDD-F8 transgene were also analyzed. Similar to the treatment of Example 3, F8 KO male mice were injected with AAV8-SaCas9-gRNA1 (SEQ ID NO: 3) and AAV8-BDD-F8 (SEQ ID NO: 4) donor viruses at a ratio of 1:8 with total viral escalating dosages from $4\times10^{11}$~$5\times10^{13}$.

1. Clotting Recovery

Figure 5:
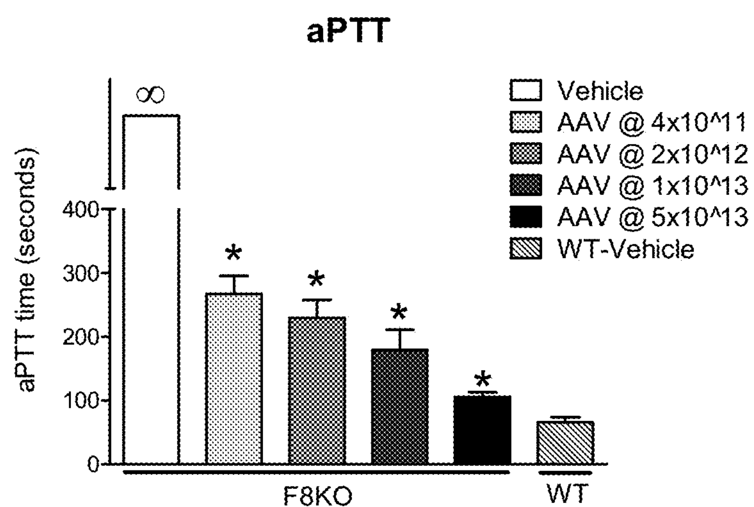
FIG. 5 shows F8 Knock-In recovers clotting in a hemophilia mouse model. Results were shown in *P<0.05 vs. F8 KO with vehicle or WT with vehicle, n=3-5 mice per group.

Mouse plasma was collected 4 weeks after injection and subjected to an activated partial thromboplastin time (aPTT) coagulation assay with Thermo Scientific™ Pacific Hemostasis™ Activated Partial Thromboplastin Time aPTT-XL kit (cat #110402). The results showed that F8 KI recovered clotting in the hemophilia mouse model (see FIG. 5).

2. Reduction in Bleeding

Figure 6A:
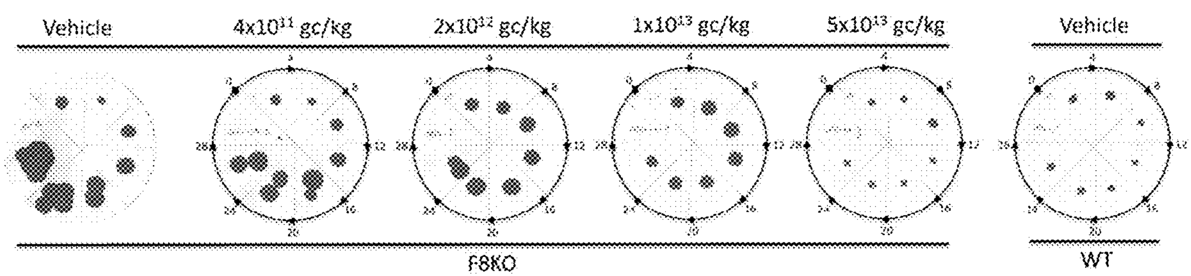
FIGS. 6A-6C show F8 Knock-In reduced bleeding in a hemophilia mouse model. Upper panel
Figure 6B:
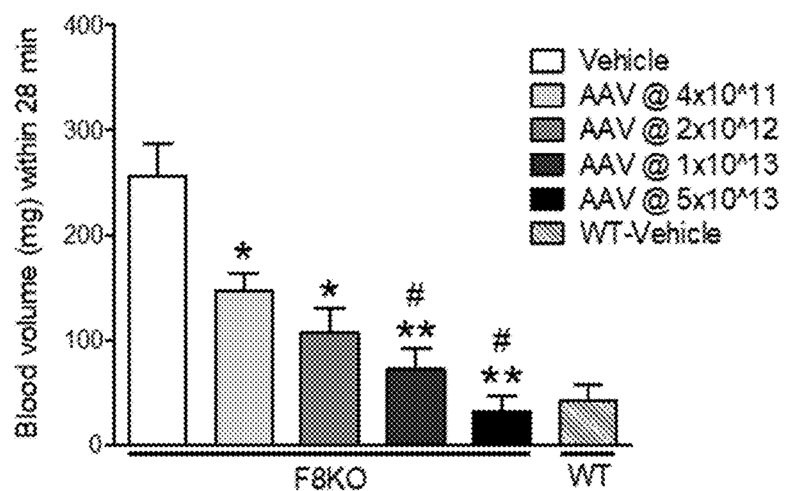
Figure 6C:
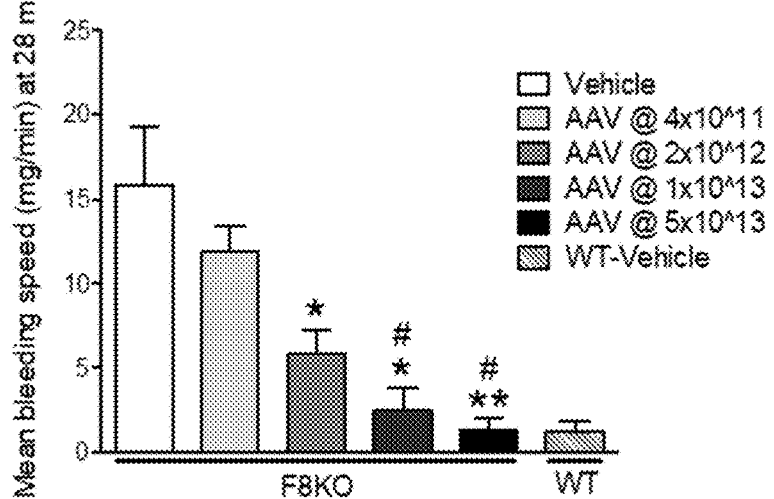

Tail bleeding was measured 4 weeks after injection. The total blood loss during the first 30 minutes and bleeding speed was calculated. Results were shown in FIG. 6, indicating that F8 KI can reduce bleeding in the hemophilia mouse model.

The above results implicated that the inserted BDD F8 transgene is functional.

What is claimed is:

1. A method of inserting a polynucleotide sequence encoding B domain deleted Factor VIII into a genome of a cell, the method comprising:

generating a DNA double-strand break at a target location of the genome via introducing into the cell a composition comprising a CRISPR-associated (Cas) nuclease and a CRISPR-Cas guide RNA directed to the target location; and introducing into said cell an adeno-associated virus (AAV), wherein said AAV comprises a nucleic acid comprising the polynucleotide sequence encoding B domain deleted Factor VIII or the complementary sequence thereof, wherein the nucleic acid does not comprise a homologous arm corresponding to the target site, and wherein the polynucleotide sequence is flanked by a sequence targeted by the CRISPR-Cas guide RNA.

2. The method of claim 1, wherein the target site is within a coding region, a safe-harbor locus or a non-coding region.

3. The method of claim 1, wherein the cell is a human cell.

4. The method of claim 1, wherein the cell is in vivo.

5. The method of claim 1, wherein the cell is from a human subject having hemophilia.

6. The method of claim 1, wherein the target location comprises a sequence of SEQ ID NO: 5.

7. The method of claim 1, wherein the B domain deleted Factor VIII has a sequence of SEQ ID NO: 1.

8. The method of claim 1, wherein the sequence encoding the B domain deleted Factor VIII has a sequence of SEQ ID NO: 2.

9. The method of claim 1, wherein the nucleic acid comprising the polynucleotide sequence encoding the B domain deleted Factor VIII has a sequence of SEQ ID NO: 4.

10. The method of claim 1, wherein the CRISPR-associated (Cas) nuclease is introduced into the cell via a vector having a sequence of SEQ ID NO: 3.

* * * * *

SEQUENCE LISTING

```
<160> NUMBER OF SEQ ID NOS: 7

<210> SEQ ID NO 1
<211> LENGTH: 1473
<212> TYPE: PRT
<213> ORGANISM: Artificial Sequence
<220> FEATURE:
<223> OTHER INFORMATION: BDD F8

<400> SEQUENCE: 1

Gln Ile Glu Leu Ser Thr Cys Phe Phe Leu Cys Leu Leu Arg Phe Cys
1               5                   10                  15
```

```
Phe Ser Ala Thr Arg Arg Tyr Tyr Leu Gly Ala Val Glu Leu Ser Trp
            20                  25                  30

Asp Tyr Met Gln Ser Asp Leu Gly Glu Leu Pro Val Asp Ala Arg Phe
        35                  40                  45

Pro Pro Arg Val Pro Lys Ser Phe Pro Phe Asn Thr Ser Val Val Tyr
    50                  55                  60

Lys Lys Thr Leu Phe Val Glu Phe Thr Asp His Leu Phe Asn Ile Ala
65                  70                  75                  80

Lys Pro Arg Pro Pro Trp Met Gly Leu Leu Gly Pro Thr Ile Gln Ala
                85                  90                  95

Glu Val Tyr Asp Thr Val Val Ile Thr Leu Lys Asn Met Ala Ser His
            100                 105                 110

Pro Val Ser Leu His Ala Val Gly Val Ser Tyr Trp Lys Ala Ser Glu
        115                 120                 125

Gly Ala Glu Tyr Asp Asp Gln Thr Ser Gln Arg Glu Lys Glu Asp Asp
    130                 135                 140

Lys Val Phe Pro Gly Gly Ser His Thr Tyr Val Trp Gln Val Leu Lys
145                 150                 155                 160

Glu Asn Gly Pro Met Ala Ser Asp Pro Leu Cys Leu Thr Tyr Ser Tyr
                165                 170                 175

Leu Ser His Val Asp Leu Val Lys Asp Leu Asn Ser Gly Leu Ile Gly
            180                 185                 190

Ala Leu Leu Val Cys Arg Glu Gly Ser Leu Ala Lys Glu Lys Thr Gln
        195                 200                 205

Thr Leu His Lys Phe Ile Leu Leu Phe Ala Val Phe Asp Glu Gly Lys
    210                 215                 220

Ser Trp His Ser Glu Thr Lys Asn Ser Leu Met Gln Asp Arg Asp Ala
225                 230                 235                 240

Ala Ser Ala Arg Ala Trp Pro Lys Met His Thr Val Asn Gly Tyr Val
                245                 250                 255

Asn Arg Ser Leu Pro Gly Leu Ile Gly Cys His Arg Lys Ser Val Tyr
            260                 265                 270

Trp His Val Ile Gly Met Gly Thr Thr Pro Glu Val His Ser Ile Phe
        275                 280                 285

Leu Glu Gly His Thr Phe Leu Val Arg Asn His Arg Gln Ala Ser Leu
    290                 295                 300

Glu Ile Ser Pro Ile Thr Phe Leu Thr Ala Gln Thr Leu Leu Met Asp
305                 310                 315                 320

Leu Gly Gln Phe Leu Leu Phe Cys His Ile Ser Ser His Gln His Asp
                325                 330                 335

Gly Met Glu Ala Tyr Val Lys Val Asp Ser Cys Pro Glu Glu Pro Gln
            340                 345                 350

Leu Arg Met Lys Asn Asn Glu Glu Ala Glu Asp Tyr Asp Asp Asp Leu
        355                 360                 365

Thr Asp Ser Glu Met Asp Val Val Arg Phe Asp Asp Asp Asn Ser Pro
    370                 375                 380

Ser Phe Ile Gln Ile Arg Ser Val Ala Lys Lys His Pro Lys Thr Trp
385                 390                 395                 400

Val His Tyr Ile Ala Ala Glu Glu Glu Asp Trp Asp Tyr Ala Pro Leu
                405                 410                 415

Val Leu Ala Pro Asp Asp Arg Ser Tyr Lys Ser Gln Tyr Leu Asn Asn
            420                 425                 430
```

```
Gly Pro Gln Arg Ile Gly Arg Lys Tyr Lys Lys Val Arg Phe Met Ala
        435                 440                 445

Tyr Thr Asp Glu Thr Phe Lys Thr Arg Glu Ala Ile Gln His Glu Ser
    450                 455                 460

Gly Ile Leu Gly Pro Leu Leu Tyr Gly Glu Val Gly Asp Thr Leu Leu
465                 470                 475                 480

Ile Ile Phe Lys Asn Gln Ala Ser Arg Pro Tyr Asn Ile Tyr Pro His
                485                 490                 495

Gly Ile Thr Asp Val Arg Pro Leu Tyr Ser Arg Arg Leu Pro Lys Gly
            500                 505                 510

Val Lys His Leu Lys Asp Phe Pro Ile Leu Pro Gly Glu Ile Phe Lys
        515                 520                 525

Tyr Lys Trp Thr Val Thr Val Glu Asp Gly Pro Thr Lys Ser Asp Pro
    530                 535                 540

Arg Cys Leu Thr Arg Tyr Tyr Ser Ser Phe Val Asn Met Glu Arg Asp
545                 550                 555                 560

Leu Ala Ser Gly Leu Ile Gly Pro Leu Leu Ile Cys Tyr Lys Glu Ser
                565                 570                 575

Val Asp Gln Arg Gly Asn Gln Ile Met Ser Asp Lys Arg Asn Val Ile
            580                 585                 590

Leu Phe Ser Val Phe Asp Glu Asn Arg Ser Trp Tyr Leu Thr Glu Asn
        595                 600                 605

Ile Gln Arg Phe Leu Pro Asn Pro Ala Gly Val Gln Leu Glu Asp Pro
    610                 615                 620

Glu Phe Gln Ala Ser Asn Ile Met His Ser Ile Asn Gly Tyr Val Phe
625                 630                 635                 640

Asp Ser Leu Gln Leu Ser Val Cys Leu His Glu Val Ala Tyr Trp Tyr
                645                 650                 655

Ile Leu Ser Ile Gly Ala Gln Thr Asp Phe Leu Ser Val Phe Phe Ser
            660                 665                 670

Gly Tyr Thr Phe Lys His Lys Met Val Tyr Glu Asp Thr Leu Thr Leu
        675                 680                 685

Phe Pro Phe Ser Gly Glu Thr Val Phe Met Ser Met Glu Asn Pro Gly
    690                 695                 700

Leu Trp Ile Leu Gly Cys His Asn Ser Asp Phe Arg Asn Arg Gly Met
705                 710                 715                 720

Thr Ala Leu Leu Lys Val Ser Ser Cys Asp Lys Asn Thr Gly Asp Tyr
                725                 730                 735

Tyr Glu Asp Ser Tyr Glu Asp Ile Ser Ala Tyr Leu Leu Ser Lys Asn
            740                 745                 750

Asn Ala Ile Glu Pro Arg Ser Phe Ser Gln Asn Ala Thr Asn Val Ser
        755                 760                 765

Asn Asn Ser Asn Thr Ser Asn Asp Ser Asn Val Ser Pro Pro Val Leu
    770                 775                 780

Lys His His Gln Arg Glu Ile Thr Arg Thr Thr Leu Gln Ser Asp Gln
785                 790                 795                 800

Glu Glu Ile Asp Tyr Asp Asp Thr Ile Ser Val Glu Met Lys Lys Glu
                805                 810                 815

Asp Phe Asp Ile Tyr Asp Glu Asp Glu Asn Gln Ser Pro Arg Ser Phe
            820                 825                 830

Gln Lys Lys Thr Arg His Tyr Phe Ile Ala Ala Val Glu Arg Leu Trp
        835                 840                 845
```

```
Asp Tyr Gly Met Ser Ser Ser Pro His Val Leu Arg Asn Arg Ala Gln
    850                 855                 860

Ser Gly Ser Val Pro Gln Phe Lys Lys Val Val Phe Gln Glu Phe Thr
865                 870                 875                 880

Asp Gly Ser Phe Thr Gln Pro Leu Tyr Arg Gly Glu Leu Asn Glu His
                885                 890                 895

Leu Gly Leu Leu Gly Pro Tyr Ile Arg Ala Glu Val Glu Asp Asn Ile
            900                 905                 910

Met Val Thr Phe Arg Asn Gln Ala Ser Arg Pro Tyr Ser Phe Tyr Ser
        915                 920                 925

Ser Leu Ile Ser Tyr Glu Glu Asp Gln Arg Gln Gly Ala Glu Pro Arg
    930                 935                 940

Lys Asn Phe Val Lys Pro Asn Glu Thr Lys Thr Tyr Phe Trp Lys Val
945                 950                 955                 960

Gln His His Met Ala Pro Thr Lys Asp Glu Phe Asp Cys Lys Ala Trp
                965                 970                 975

Ala Tyr Phe Ser Asp Val Asp Leu Glu Lys Asp Val His Ser Gly Leu
            980                 985                 990

Ile Gly Pro Leu Leu Val Cys His  Thr Asn Thr Leu Asn  Pro Ala His
        995                 1000                1005

Gly Arg  Gln Val Thr Val Gln  Glu Phe Ala Leu Phe  Phe Thr Ile
    1010                1015                1020

Phe Asp  Glu Thr Lys Ser Trp  Tyr Phe Thr Glu Asn  Met Glu Arg
    1025                1030                1035

Asn Cys  Arg Ala Pro Cys Asn  Ile Gln Met Glu Asp  Pro Thr Phe
    1040                1045                1050

Lys Glu  Asn Tyr Arg Phe His  Ala Ile Asn Gly Tyr  Ile Met Asp
    1055                1060                1065

Thr Leu  Pro Gly Leu Val Met  Ala Gln Asp Gln Arg  Ile Arg Trp
    1070                1075                1080

Tyr Leu  Leu Ser Met Gly Ser  Asn Glu Asn Ile His  Ser Ile His
    1085                1090                1095

Phe Ser  Gly His Val Phe Thr  Val Arg Lys Lys Glu  Glu Tyr Lys
    1100                1105                1110

Met Ala  Leu Tyr Asn Leu Tyr  Pro Gly Val Phe Glu  Thr Val Glu
    1115                1120                1125

Met Leu  Pro Ser Lys Ala Gly  Ile Trp Arg Val Glu  Cys Leu Ile
    1130                1135                1140

Gly Glu  His Leu His Ala Gly  Met Ser Thr Leu Phe  Leu Val Tyr
    1145                1150                1155

Ser Asn  Lys Cys Gln Thr Pro  Leu Gly Met Ala Ser  Gly His Ile
    1160                1165                1170

Arg Asp  Phe Gln Ile Thr Ala  Ser Gly Gln Tyr Gly  Gln Trp Ala
    1175                1180                1185

Pro Lys  Leu Ala Arg Leu His  Tyr Ser Gly Ser Ile  Asn Ala Trp
    1190                1195                1200

Ser Thr  Lys Glu Pro Phe Ser  Trp Ile Lys Val Asp  Leu Leu Ala
    1205                1210                1215

Pro Met  Ile Ile His Gly Ile  Lys Thr Gln Gly Ala  Arg Gln Lys
    1220                1225                1230

Phe Ser  Ser Leu Tyr Ile Ser  Gln Phe Ile Ile Met  Tyr Ser Leu
    1235                1240                1245
```

```
Asp Gly  Lys Lys Trp Gln Thr  Tyr Arg Gly Asn Ser  Thr Gly Thr
    1250                 1255                 1260

Leu Met  Val Phe Phe Gly Asn  Val Asp Ser Ser Gly  Ile Lys His
    1265                 1270                 1275

Asn Ile  Phe Asn Pro Pro Ile  Ile Ala Arg Tyr Ile  Arg Leu His
    1280                 1285                 1290

Pro Thr  His Tyr Ser Ile Arg  Ser Thr Leu Arg Met  Glu Leu Met
    1295                 1300                 1305

Gly Cys  Asp Leu Asn Ser Cys  Ser Met Pro Leu Gly  Met Glu Ser
    1310                 1315                 1320

Lys Ala  Ile Ser Asp Ala Gln  Ile Thr Ala Ser Ser  Tyr Phe Thr
    1325                 1330                 1335

Asn Met  Phe Ala Thr Trp Ser  Pro Ser Lys Ala Arg  Leu His Leu
    1340                 1345                 1350

Gln Gly  Arg Ser Asn Ala Trp  Arg Pro Gln Val Asn  Asn Pro Lys
    1355                 1360                 1365

Glu Trp  Leu Gln Val Asp Phe  Gln Lys Thr Met Lys  Val Thr Gly
    1370                 1375                 1380

Val Thr  Thr Gln Gly Val Lys  Ser Leu Leu Thr Ser  Met Tyr Val
    1385                 1390                 1395

Lys Glu  Phe Leu Ile Ser Ser  Ser Gln Asp Gly His  Gln Trp Thr
    1400                 1405                 1410

Leu Phe  Phe Gln Asn Gly Lys  Val Lys Val Phe Gln  Gly Asn Gln
    1415                 1420                 1425

Asp Ser  Phe Thr Pro Val Val  Asn Ser Leu Asp Pro  Pro Leu Leu
    1430                 1435                 1440

Thr Arg  Tyr Leu Arg Ile His  Pro Gln Ser Trp Val  His Gln Ile
    1445                 1450                 1455

Ala Leu  Arg Met Glu Val Leu  Gly Cys Glu Ala Gln  Asp Leu Tyr
    1460                 1465                 1470
```

```
<210> SEQ ID NO 2
<211> LENGTH: 4422
<212> TYPE: DNA
<213> ORGANISM: Artificial Sequence
<220> FEATURE:
<223> OTHER INFORMATION: BDD F8

<400> SEQUENCE: 2

cagattgagc tgtcaacttg ctttttcctg tgcctgctga gattttgttt ttccgctact     60

agaagatact acctgggggc tgtggaactg tcttgggatt acatgcagag tgacctggga    120

gagctgccag tggacgcacg atttccacct agagtcccta aatcattccc cttcaacacc    180

agcgtggtct ataagaaaac actgttcgtg gagtttactg atcacctgtt caacatcgct    240

aagcctcggc caccctggat gggactgctg ggaccaacaa tccaggcaga ggtgtacgac    300

accgtggtca ttacactgaa aaacatggcc tcacaccccg tgagcctgca tgctgtgggc    360

gtcagctact ggaaggcttc cgaaggggca gagtatgacg atcagacttc ccagagagaa    420

aaagaggacg ataaggtgtt tcctggcggg tctcatacct atgtgtggca ggtcctgaaa    480

gagaatggcc ccatggcttc cgaccctctg tgcctgacct actcttatct gagtcacgtg    540

gacctggtca aggatctgaa cagcggactg atcggagcac tgctggtgtg tagggaaggg    600

agcctggcta aggagaaaac ccagacactg cataagttca ttctgctgtt cgccgtgttt    660

gacgaaggaa aatcatggca cagcgagaca aagaatagtc tgatgcagga ccgggatgcc    720
```

-continued

```
gcttcagcca gagcttggcc caaaatgcac actgtgaacg gctacgtcaa tcgctcactg    780
cctggactga tcggctgcca ccgaaagagc gtgtattggc atgtcatcgg aatgggcacc    840
acacctgaag tgcactccat tttcctggag gggcatacct ttctggtccg caaccaccga    900
caggcctccc tggagatctc tccaattacc ttcctgacag ctcagactct gctgatggat    960
ctgggacagt tcctgctgtt ttgccacatc agctcccacc agcatgatgg catggaggcc   1020
tacgtgaaag tggacagctg tcccgaggaa cctcagctga ggatgaagaa caatgaggaa   1080
gctgaagact atgacgatga cctgaccgac tccgagatgg atgtggtccg attcgatgac   1140
gataacagcc cctcctttat ccagattaga tctgtggcca agaaacaccc taagacatgg   1200
gtccattaca tcgcagccga ggaagaggac tgggattatg caccactggt gctggcacca   1260
gacgatcgat cctacaaatc tcagtatctg aacaatggac cacagcggat tggcagaaag   1320
tacaagaaag tgaggttcat ggcttatacc gatgaaacct tcaagactcg cgaagcaatc   1380
cagcacgaga gcgggattct gggaccactg ctgtacggag aagtggggga caccctgctg   1440
atcattttta agaaccaggc cagcaggcct tacaatatct atccacatgg aattacagat   1500
gtgcgccctc tgtacagccg gagactgcca aagggcgtca aacacctgaa ggacttccca   1560
atcctgcccg gggaaatttt taagtataaa tggactgtca ccgtcgagga tggccccact   1620
aagagcgacc ctaggtgcct gacccgctac tattctagtt tcgtgaatat ggaaagggat   1680
ctggccagcg gactgatcgg cccactgctg atttgttaca aagagagcgt ggatcagaga   1740
ggcaaccaga tcatgtccga caagaggaat gtgattctgt tcagtgtctt tgacgaaaac   1800
cggtcatggt atctgaccga gaacatccag agattcctgc ctaatccagc cggagtgcag   1860
ctggaagatc ctgagtttca ggcttctaac atcatgcata gtattaatgg ctacgtgttc   1920
gacagtctgc agctgtcagt gtgtctgcac gaggtcgctt actggtatat cctgagcatt   1980
ggagcacaga cagatttcct gagcgtgttc ttttccggct acacttttaa gcataaaatg   2040
gtgtatgagg acacactgac tctgttcccc ttcagcggcg aaaccgtgtt tatgtccatg   2100
gagaatcccg ggctgtggat cctgggatgc cacaacagcg atttcaggaa tcgcgggatg   2160
actgccctgc tgaaagtgtc aagctgtgac aagaacaccg gagactacta tgaagattca   2220
tacgaggaca tcagcgcata tctgctgtcc aaaaacaatg ccattgaacc caggtctttt   2280
agtcagaatg cgaccaacgt gagcaacaac agcaacacca gcaacgatag caacgtgagc   2340
cctccagtgc tgaagcacca ccagcgcgag atcacccgca ctaccctgca gagtgatcag   2400
gaagagatcg actacgacga tacaatttct gtggaaatga agaaagagga cttcgatatc   2460
tatgacgaag atgagaacca gagtcctcga tcattccaga agaaaacccg gcattacttt   2520
attgctgcag tggagcgcct gtgggattat ggcatgtcct ctagtcctca cgtgctgcga   2580
aatcgggccc agtcagggag cgtcccacag ttcaagaaag tggtcttcca ggagtttaca   2640
gacggatcct ttactcagcc actgtaccgg ggcgaactga acgagcacct ggggctgctg   2700
ggaccctata tcagagctga agtggaggat aacattatgg tcaccttcag aaatcaggca   2760
tctaggcctt acagttttta ttcaagcctg atctcttacg aagaggacca gaggcaggga   2820
gcagaaccac gaaaaaactt cgtgaagcct aatgagacca aaacatactt ttggaaggtg   2880
cagcaccata tggccccaac aaaagacgaa ttcgattgca aggcatgggc ctatttttct   2940
gacgtggatc tggagaagga cgtccacagt ggcctgatcg ggccactgct ggtgtgtcat   3000
actaacaccc tgaatcccgc acacggcagg caggtcactg tccaggaatt cgccctgttc   3060
tttaccatct ttgatgagac aaaaagctgg tacttcaccg aaaacatgga gcgaaattgc   3120
```

cgggctccat gtaatattca gatggaagac cccacattca aggagaacta ccgctttcat 3180
gccatcaatg ggtatattat ggatactctg cccggactgg tcatggctca ggaccagaga 3240
atcaggtggt acctgctgag catggggtcc aacgagaata tccactcaat tcatttcagc 3300
ggacacgtgt ttactgtccg gaagaaagaa gagtataaaa tggccctgta caacctgtat 3360
cccggcgtgt tcgaaaccgt cgagatgctg cctagcaagg cagggatctg gagagtggaa 3420
tgcctgattg gggagcacct gcatgccgga atgtctaccc tgtttctggt gtacagtaat 3480
aagtgtcaga caccccctggg gatggcttcc ggacatatcc gggatttcca gattaccgca 3540
tctggacagt acggccagtg ggcccctaag ctggctagac tgcactattc cgggtctatc 3600
aacgcttggt ccacaaaaga gcctttctct tggattaagg tggacctgct ggcaccaatg 3660
atcattcatg gcatcaaaac tcagggggcc aggcagaagt tctcctctct gtacatctca 3720
cagtttatca tcatgtacag cctggatggc aagaaatggc agacataccg cggcaatagc 3780
acagggactc tgatggtgtt ctttggcaac gtggacagtt cagggatcaa gcacaacatt 3840
ttcaatcccc ctatcattgc tagatacatc aggctgcacc caacccatta ttctattcga 3900
agtacactgc ggatggaact gatggggtgc gatctgaaca gttgttcaat gcccctggga 3960
atggagtcca aggcaatctc tgacgcccag attaccgcta gctcctactt cactaatatg 4020
tttgctacct ggagcccctc caaagcacga ctgcatctgc agggacgaag caacgcatgg 4080
cgaccacagg tgaacaatcc caaggagtgg ctgcaggtcg attttcagaa aactatgaag 4140
gtgaccggag tcacaactca gggcgtgaaa agtctgctga cctcaatgta cgtcaaggag 4200
ttcctgatct ctagttcaca ggacggccac cagtggacac tgttctttca gaacggaaag 4260
gtgaaagtct tccagggcaa tcaggattcc tttacacctg tggtcaactc tctggaccca 4320
cccctgctga ctcgctacct gcgaatccac ccacagtcct gggtgcatca gattgcactg 4380
agaatggaag tcctgggctg cgaggcccag gacctgtatt ga 4422

<210> SEQ ID NO 3
<211> LENGTH: 7294
<212> TYPE: DNA
<213> ORGANISM: Artificial Sequence
<220> FEATURE:
<223> OTHER INFORMATION: SaCas9 AAV vector

<400> SEQUENCE: 3
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggcctcta gactcgaggg gctggaagct acctttgaca tcatttcctc 180
tgcgaatgca tgtataattt ctacagaacc tattagaaag gatcacccag cctctgcttt 240
tgtacaactt tcccttaaaa aactgccaat tccactgctg tttggcccaa tagtgagaac 300
tttttcctgc tgcctcttgg tgcttttgcc tatggcccct attctgcctg ctgaagacac 360
tcttgccagc atggacttaa acccctccag ctctgacaat cctctttctc ttttgtttta 420
catgaagggt ctggcagcca aagcaatcac tcaaagttca aaccttatca ttttttgctt 480
tgttcctctt ggccttggtt ttgtacatca gctttgaaaa taccatccca gggttaatgc 540
tggggttaat ttataactaa gagtgctcta gttttgcaat acaggacatg ctataaaaat 600
ggaaagatac cggtgccacc atggccccaa agaagaagcg gaaggtcggt atccacggag 660
tcccagcagc caagcggaac tacatcctgg gcctggacat cggcatcacc agcgtgggct 720

-continued

```
acggcatcat cgactacgag acacgggacg tgatcgatgc cggcgtgcgg ctgttcaaag    780

aggccaacgt ggaaaacaac gagggcaggc ggagcaagag aggcgccaga aggctgaagc    840

ggcggaggcg gcatagaatc cagagagtga agaagctgct gttcgactac aacctgctga    900

ccgaccacag cgagctgagc ggcatcaacc cctacgaggc cagagtgaag ggcctgagcc    960

agaagctgag cgaggaagag ttctctgccg ccctgctgca cctggccaag agaagaggcg   1020

tgcacaacgt gaacgaggtg gaagaggaca ccggcaacga gctgtccacc agagagcaga   1080

tcagccggaa cagcaaggcc ctggaagaga aatacgtggc cgaactgcag ctggaacggc   1140

tgaagaaaga cggcgaagtg cggggcagca tcaacagatt caagaccagc gactacgtga   1200

aagaagccaa acagctgctg aaggtgcaga aggcctacca ccagctggac cagagcttca   1260

tcgacaccta catcgacctg ctggaaaccc ggcggaccta ctatgaggga cctggcgagg   1320

gcagcccctt cggctggaag gacatcaaag aatggtacga gatgctgatg ggccactgca   1380

cctacttccc cgaggaactg cggagcgtga agtacgccta caacgccgac ctgtacaacg   1440

ccctgaacga cctgaacaat ctcgtgatca ccagggacga gaacgagaag ctggaatatt   1500

acgagaagtt ccagatcatc gagaacgtgt tcaagcagaa gaagaagccc accctgaagc   1560

agatcgccaa agaaatcctc gtgaacgaag aggatattaa gggctacaga gtgaccagca   1620

ccggcaagcc cgagttcacc aacctgaagg tgtaccacga catcaaggac attaccgccc   1680

ggaaagagat tattgagaac gccgagctgc tggatcagat tgccaagatc ctgaccatct   1740

accagagcag cgaggacatc caggaagaac tgaccaatct gaactccgag ctgacccagg   1800

aagagatcga gcagatctct aatctgaagg gctataccgg cacccacaac ctgagcctga   1860

aggccatcaa cctgatcctg gacgagctgt ggcacaccaa cgacaaccag atcgctatct   1920

tcaaccggct gaagctggtg cccaagaagg tggacctgtc ccagcagaaa gagatcccca   1980

ccaccctggt ggacgacttc atcctgagcc ccgtcgtgaa gagaagcttc atccagagca   2040

tcaaagtgat caacgccatc atcaagaagt acggcctgcc caacgacatc attatcgagc   2100

tggcccgcga gaagaactcc aaggacgccc agaaaatgat caacgagatg cagaagcgga   2160

accggcagac caacgagcgg atcgaggaaa tcatccggac caccggcaaa gagaacgcca   2220

agtacctgat cgagaagatc aagctgcacg acatgcagga aggcaagtgc ctgtacagcc   2280

tggaagccat ccctctggaa gatctgctga acaacccctt caactatgag gtggaccaca   2340

tcatccccag aagcgtgtcc ttcgacaaca gcttcaacaa caaggtgctc gtgaagcagg   2400

aagaaaacag caagaagggc aaccggaccc cattccagta cctgagcagc agcgacagca   2460

agatcagcta cgaaaccttc aagaagcaca tcctgaatct ggccaagggc aagggcagaa   2520

tcagcaagac caagaaagag tatctgctgg aagaacggga catcaacagg ttctccgtgc   2580

agaaagactt catcaaccgg aacctggtgg ataccagata cgccaccaga ggcctgatga   2640

acctgctgcg gagctacttc agagtgaaca acctggacgt gaaagtgaag tccatcaatg   2700

gcggcttcac cagctttctg cggcggaagt ggaagtttaa gaaagagcgg aacaaggggt   2760

acaagcacca cgccgaggac gccctgatca ttgccaacgc cgatttcatc ttcaaagagt   2820

ggaagaaact ggacaaggcc aaaaaagtga tggaaaacca gatgttcgag gaaaagcagg   2880

ccgagagcat gcccgagatc gaaaccgagc aggagtacaa agagatcttc atcacccccc   2940

accagatcaa gcacattaag gacttcaagg actacaagta cagccaccgg gtggacaaga   3000

agcctaatag agagctgatt aacgacaccc tgtactccac ccggaaggac gacaagggca   3060

acaccctgat cgtgaacaat ctgaacggcc tgtacgacaa ggacaatgac aagctgaaaa   3120
```

```
agctgatcaa caagagcccc gaaaagctgc tgatgtacca ccacgacccc cagacctacc   3180

agaaactgaa gctgattatg gaacagtacg gcgacgagaa gaatcccctg tacaagtact   3240

acgaggaaac cgggaactac ctgaccaagt actccaaaaa ggacaacggc cccgtgatca   3300

agaagattaa gtattacggc aacaaactga acgcccatct ggacatcacc gacgactacc   3360

ccaacagcag aaacaaggtc gtgaagctgt ccctgaagcc ctacagattc gacgtgtacc   3420

tggacaatgg cgtgtacaag ttcgtgaccg tgaagaatct ggatgtgatc aaaaaagaaa   3480

actactacga agtgaatagc aagtgctatg aggaagctaa gaagctgaag aagatcagca   3540

accaggccga gtttatcgcc tccttctaca acaacgatct gatcaagatc aacggcgagc   3600

tgtatagagt gatcggcgtg aacaacgacc tgctgaaccg gatcgaagtg aacatgatcg   3660

acatcaccta ccgcgagtac ctggaaaaca tgaacgacaa gaggcccccc aggatcatta   3720

agacaatcgc ctccaagacc cagagcatta agaagtacag cacagacatt ctgggcaacc   3780

tgtatgaagt gaaatctaag aagcaccctc agatcatcaa aaagggcaaa aggccggcgg   3840

ccacgaaaaa ggccggccag gcaaaaaaga aaaagggatc ctacccatac gatgttccag   3900

attacgctag cggcttcgcc aacgagcttg gacccaggtt gatgggaaag taagaattcc   3960

tagagctcgc tgatcagcct cgactgtgcc ttctagttgc cagccatctg ttgtttgccc   4020

ctcccccgtg ccttccttga ccctggaagg tgccactccc actgtccttt cctaataaaa   4080

tgaggaaatt gcatcgcatt gtctgagtag gtgtcattct attctggggg gtggggtggg   4140

gcaggacagc aagggggagg attgggaaga gaatagcagg catgctgggg aggtaccaaa   4200

aatctcgcca acaagttgac gagataaaca cggcattttg ccttgtttta gtagattctg   4260

tttccagagt actaaaacgg ctttgcaagt atttctaacg gtgtttcgtc ctttccacaa   4320

gatatataaa gccaagaaat cgaaatactt tcaagttacg gtaagcatat gatagtccat   4380

tttaaaacat aattttaaaa ctgcaaacta cccaagaaat tattactttc tacgtcacgt   4440

attttgtact aatatctttg tgtttacagt caaattaatt ccaattatct ctctaacagc   4500

cttgtatcgt atatgcaaat atgaaggaat catgggaaat aggccctcgc ggccgcagga   4560

acccctagtg atggagttgg ccactccctc tctgcgcgct cgctcgctca ctgaggccgg   4620

gcgaccaaag gtcgcccgac gcccgggctt tgcccgggcg gcctcagtga gcgagcgagc   4680

gcgcagctgc ctgcaggggc gcctgatgcg gtattttctc cttacgcatc tgtgcggtat   4740

ttcacaccgc atacgtcaaa gcaaccatag tacgcgccct gtagcggcgc attaagcgcg   4800

gcgggtgtgg tggttacgcg cagcgtgacc gctacacttg ccagcgccct agcgcccgct   4860

cctttcgctt tcttcccttc ctttctcgcc acgttcgccg gctttccccg tcaagctcta   4920

aatcgggggc tccctttagg gttccgattt agtgctttac ggcacctcga ccccaaaaaa   4980

cttgatttgg gtgatggttc acgtagtggg ccatcgccct gatagacggt ttttcgccct   5040

ttgacgttgg agtccacgtt ctttaatagt ggactcttgt tccaaactgg aacaacactc   5100

aaccctatct cgggctattc ttttgattta taagggattt tgccgatttc ggcctattgg   5160

ttaaaaaatg agctgattta acaaaaattt aacgcgaatt ttaacaaaat attaacgttt   5220

acaattttat ggtgcactct cagtacaatc tgctctgatg ccgcatagtt aagccagccc   5280

cgacacccgc caacacccgc tgacgcgccc tgacgggctt gtctgctccc ggcatccgct   5340

tacagacaag ctgtgaccgt ctccgggagc tgcatgtgtc agaggttttc accgtcatca   5400

ccgaaacgcg cgagacgaaa gggcctcgtg atacgcctat ttttataggt taatgtcatg   5460
```

```
ataataatgg tttcttagac gtcaggtggc acttttcggg gaaatgtgcg cggaacccct   5520

atttgtttat ttttctaaat acattcaaat atgtatccgc tcatgagaca ataaccctga   5580

taaatgcttc aataatattg aaaaaggaag agtatgagta ttcaacattt ccgtgtcgcc   5640

cttattccct tttttgcggc attttgcctt cctgtttttg ctcacccaga aacgctggtg   5700

aaagtaaaag atgctgaaga tcagttgggt gcacgagtgg gttacatcga actggatctc   5760

aacagcggta agatccttga gagttttcgc cccgaagaac gttttccaat gatgagcact   5820

tttaaagttc tgctatgtgg cgcggtatta tcccgtattg acgccgggca agagcaactc   5880

ggtcgccgca tacactattc tcagaatgac ttggttgagt actcaccagt cacagaaaag   5940

catcttacgg atggcatgac agtaagagaa ttatgcagtg ctgccataac catgagtgat   6000

aacactgcgg ccaacttact tctgacaacg atcggaggac cgaaggagct aaccgctttt   6060

ttgcacaaca tgggggatca tgtaactcgc cttgatcgtt gggaaccgga gctgaatgaa   6120

gccataccaa acgacgagcg tgacaccacg atgcctgtag caatggcaac aacgttgcgc   6180

aaactattaa ctggcgaact acttactcta gcttcccggc aacaattaat agactggatg   6240

gaggcggata aagttgcagg accacttctg cgctcggccc ttccggctgg ctggtttatt   6300

gctgataaat ctggagccgg tgagcgtgga agccgcggta tcattgcagc actggggcca   6360

gatggtaagc cctcccgtat cgtagttatc tacacgacgg ggagtcaggc aactatggat   6420

gaacgaaata gacagatcgc tgagataggt gcctcactga ttaagcattg gtaactgtca   6480

gaccaagttt actcatatat actttagatt gatttaaaac ttcattttta atttaaaagg   6540

atctaggtga agatcctttt tgataatctc atgaccaaaa tcccttaacg tgagttttcg   6600

ttccactgag cgtcagaccc cgtagaaaag atcaaaggat cttcttgaga tccttttttt   6660

ctgcgcgtaa tctgctgctt gcaaacaaaa aaaccaccgc taccagcggt ggtttgtttg   6720

ccggatcaag agctaccaac tctttttccg aaggtaactg gcttcagcag agcgcagata   6780

ccaaatactg tccttctagt gtagccgtag ttaggccacc acttcaagaa ctctgtagca   6840

ccgcctacat acctcgctct gctaatcctg ttaccagtgg ctgctgccag tggcgataag   6900

tcgtgtctta ccgggttgga ctcaagacga tagttaccgg ataaggcgca gcggtcgggc   6960

tgaacggggg gttcgtgcac acagcccagc ttggagcgaa cgacctacac cgaactgaga   7020

tacctacagc gtgagctatg agaaagcgcc acgcttcccg aagggagaaa ggcggacagg   7080

tatccggtaa gcggcagggt cggaacagga gagcgcacga gggagcttcc agggggaaac   7140

gcctggtatc tttatagtcc tgtcgggttt cgccacctct gacttgagcg tcgatttttg   7200

tgatgctcgt caggggggcg gagcctatgg aaaaacgcca gcaacgcggc ctttttacgg   7260

ttcctggcct tttgctggcc ttttgctcac atgt                              7294
```

<210> SEQ ID NO 4
<211> LENGTH: 7532
<212> TYPE: DNA
<213> ORGANISM: Artificial Sequence
<220> FEATURE:
<223> OTHER INFORMATION: BDD-F8 donor AAV vector

<400> SEQUENCE: 4

```
gcattaagcg cggcgggtgt ggtggttacg cgcagcgtga ccgctacact tgccagcgcc     60

ctagcgcccg ctcctttcgc tttcttccct tcctttctcg ccacgttcgc cggctttccc    120

cgtcaagctc taaatcgggg gctcccttta gggttccgat ttagtgcttt acggcacctc    180

gaccccaaaa aacttgattt gggtgatggt tcacgtagtg ggccatcgcc ctgatagacg    240
```

```
gtttttcgcc ctttgacgtt ggagtccacg ttctttaata gtggactctt gttccaaact    300
ggaacaacac tcaaccctat ctcgggctat tcttttgatt tataagggat tttgccgatt    360
tcggcctatt ggttaaaaaa tgagctgatt taacaaaaat ttaacgcgaa ttttaacaaa    420
atattaacgt ttacaatttt atggtgcact ctcagtacaa tctgctctga tgccgcatag    480
ttaagccagc cccgacaccc gccaacaccc gctgacgcgc cctgacgggc ttgtctgctc    540
ccggcatccg cttacagaca agctgtgacc gtctccggga gctgcatgtg tcagaggttt    600
tcaccgtcat caccgaaacg cgcgagacga aagggcctcg tgatacgcct atttttatag    660
gttaatgtca tgataataat ggtttcttag acgtcaggtg gcacttttcg gggaaatgtg    720
cgcggaaccc ctatttgttt atttttctaa atacattcaa atatgtatcc gctcatgaga    780
caataaccct gataaatgct tcaataatat tgaaaaagga agagtatgag tattcaacat    840
ttccgtgtcg cccttattcc cttttttgcg gcattttgcc ttcctgtttt tgctcaccca    900
gaaacgctgg tgaaagtaaa agatgctgaa gatcagttgg gtgcacgagt gggttacatc    960
gaactggatc tcaacagcgg taagatcctt gagagttttc gccccgaaga acgttttcca   1020
atgatgagca cttttaaagt tctgctatgt ggcgcggtat tatcccgtat tgacgccggg   1080
caagagcaac tcggtcgccg catacactat tctcagaatg acttggttga gtactcacca   1140
gtcacagaaa agcatcttac ggatggcatg acagtaagag aattatgcag tgctgccata   1200
accatgagtg ataacactgc ggccaactta cttctgacaa cgatcggagg accgaaggag   1260
ctaaccgctt ttttgcacaa catgggggat catgtaactc gccttgatcg ttgggaaccg   1320
gagctgaatg aagccatacc aaacgacgag cgtgacacca cgatgcctgt agcaatggca   1380
acaacgttgc gcaaactatt aactggcgaa ctacttactc tagcttcccg gcaacaatta   1440
atagactgga tggaggcgga taaagttgca ggaccacttc tgcgctcggc ccttccggct   1500
ggctggttta ttgctgataa atctggagcc ggtgagcgtg gaagccgcgg tatcattgca   1560
gcactggggc cagatggtaa gccctcccgt atcgtagtta tctacacgac ggggagtcag   1620
gcaactatgg atgaacgaaa tagacagatc gctgagatag gtgcctcact gattaagcat   1680
tggtaactgt cagaccaagt ttactcatat atactttaga ttgatttaaa acttcatttt   1740
taatttaaaa ggatctaggt gaagatcctt tttgataatc tcatgaccaa aatcccttaa   1800
cgtgagtttt cgttccactg agcgtcagac cccgtagaaa agatcaaagg atcttcttga   1860
gatccttttt ttctgcgcgt aatctgctgc ttgcaaacaa aaaaaccacc gctaccagcg   1920
gtggtttgtt tgccggatca agagctacca actctttttc cgaaggtaac tggcttcagc   1980
agagcgcaga taccaaatac tgtccttcta gtgtagccgt agttaggcca ccacttcaag   2040
aactctgtag caccgcctac atacctcgct ctgctaatcc tgttaccagt ggctgctgcc   2100
agtggcgata agtcgtgtct taccgggttg gactcaagac gatagttacc ggataaggcg   2160
cagcggtcgg gctgaacggg gggttcgtgc acacagccca gcttggagcg aacgacctac   2220
accgaactga gatacctaca gcgtgagcta tgagaaagcg ccacgcttcc cgaagggaga   2280
aaggcggaca ggtatccggt aagcggcagg gtcggaacag gagagcgcac gagggagctt   2340
ccagggggaa acgcctggta tctttatagt cctgtcgggt ttcgccacct ctgacttgag   2400
cgtcgatttt tgtgatgctc gtcagggggg cggagcctat ggaaaaacgc cagcaacgcg   2460
gcctttttac ggttcctggc cttttgctgg ccttttgctc acatgtcctg caggcagctg   2520
cgcgctcgct cgctcactga ggccgcccgg gcgtcgggcg acctttggtc gcccggcctc   2580
```

-continued

```
agtgagcgag cgagcgcgca gagagggagt ggccaactcc atcactaggg gttcctgcgg   2640
cctctagact cgaggttaga aatacttgca aagcctagaa tgcaaatcct aacagtcctg   2700
ctaatacttt tctaacatcc atcatttctt tgttttcagg gtccaaacct tgtcactaga   2760
tgcaaagacg ccttagccgg aagcggagct actaacttca gcctgctgaa gcaggctgga   2820
gacgtggagg agaaccctgg acctcagatt gagctgtcaa cttgcttttt cctgtgcctg   2880
ctgagatttt gtttttccgc tactagaaga tactacctgg gggctgtgga actgtcttgg   2940
gattacatgc agagtgacct gggagagctg ccagtggacg cacgatttcc acctagagtc   3000
cctaaatcat tccccttcaa caccagcgtg gtctataaga aaacactgtt cgtggagttt   3060
actgatcacc tgttcaacat cgctaagcct cggccaccct ggatgggact gctgggacca   3120
acaatccagg cagaggtgta cgacaccgtg gtcattacac tgaaaaacat ggcctcacac   3180
cccgtgagcc tgcatgctgt gggcgtcagc tactggaagg cttccgaagg ggcagagtat   3240
gacgatcaga cttcccagag agaaaaagag gacgataagg tgtttcctgg cgggtctcat   3300
acctatgtgt ggcaggtcct gaaagagaat ggccccatgg cttccgaccc tctgtgcctg   3360
acctactctt atctgagtca cgtggacctg gtcaaggatc tgaacagcgg actgatcgga   3420
gcactgctgg tgtgtaggga agggagcctg gctaaggaga aaacccagac actgcataag   3480
ttcattctgc tgttcgccgt gtttgacgaa ggaaaatcat ggcacagcga gacaaagaat   3540
agtctgatgc aggaccggga tgccgcttca gccagagctt ggcccaaaat gcacactgtg   3600
aacggctacg tcaatcgctc actgcctgga ctgatcggct gccaccgaaa gagcgtgtat   3660
tggcatgtca tcggaatggg caccacacct gaagtgcact ccattttcct ggaggggcat   3720
acctttctgg tccgcaacca ccgacaggcc tccctggaga tctctccaat taccttcctg   3780
acagctcaga ctctgctgat ggatctggga cagttcctgc tgttttgcca catcagctcc   3840
caccagcatg atggcatgga ggcctacgtg aaagtggaca gctgtcccga ggaacctcag   3900
ctgaggatga agaacaatga ggaagctgaa gactatgacg atgacctgac cgactccgag   3960
atggatgtgg tccgattcga tgacgataac agcccctcct ttatccagat tagatctgtg   4020
gccaagaaac accctaagac atgggtccat tacatcgcag ccgaggaaga ggactgggat   4080
tatgcaccac tggtgctggc accagacgat cgatcctaca aatctcagta tctgaacaat   4140
ggaccacagc ggattggcag aaagtacaag aaagtgaggt tcatggctta taccgatgaa   4200
accttcaaga ctcgcgaagc aatccagcac gagagcggga ttctgggacc actgctgtac   4260
ggagaagtgg gggacaccct gctgatcatt tttaagaacc aggccagcag gccttacaat   4320
atctatccac atggaattac agatgtgcgc cctctgtaca gccggagact gccaaagggc   4380
gtcaaacacc tgaaggactt cccaatcctg cccggggaaa tttttaagta taaatggact   4440
gtcaccgtcg aggatggccc cactaagagc gaccctaggt gcctgacccg ctactattct   4500
agtttcgtga atatggaaag ggatctggcc agcggactga tcggcccact gctgatttgt   4560
tacaaagaga gcgtggatca gagaggcaac cagatcatgt ccgacaagag gaatgtgatt   4620
ctgttcagtg tctttgacga aaaccggtca tggtatctga ccgagaacat ccagagattc   4680
ctgcctaatc cagccggagt gcagctggaa gatcctgagt ttcaggcttc taacatcatg   4740
catagtatta atggctacgt gttcgacagt ctgcagctgt cagtgtgtct gcacgaggtc   4800
gcttactggt atatcctgag cattggagca cagacagatt tcctgagcgt gttcttttcc   4860
ggctacactt ttaagcataa aatggtgtat gaggacacac tgactctgtt ccccttcagc   4920
ggcgaaaccg tgtttatgtc catggagaat cccgggctgt ggatcctggg atgccacaac   4980
```

```
agcgatttca ggaatcgcgg gatgactgcc ctgctgaaag tgtcaagctg tgacaagaac   5040

accggagact actatgaaga ttcatacgag gacatcagcg catatctgct gtccaaaaac   5100

aatgccattg aacccaggtc ttttagtcag aatgcgacca acgtgagcaa caacagcaac   5160

accagcaacg atagcaacgt gagccctcca gtgctgaagc accaccagcg cgagatcacc   5220

cgcactaccc tgcagagtga tcaggaagag atcgactacg acgatacaat ttctgtggaa   5280

atgaagaaag aggacttcga tatctatgac gaagatgaga accagagtcc tcgatcattc   5340

cagaagaaaa cccggcatta ctttattgct gcagtggagc gcctgtggga ttatggcatg   5400

tcctctagtc ctcacgtgct gcgaaatcgg gcccagtcag ggagcgtccc acagttcaag   5460

aaagtggtct tccaggagtt tacagacgga tcctttactc agccactgta ccggggcgaa   5520

ctgaacgagc acctggggct gctgggaccc tatatcagag ctgaagtgga ggataacatt   5580

atggtcacct tcagaaatca ggcatctagg ccttacagtt tttattcaag cctgatctct   5640

tacgaagagg accagaggca gggagcagaa ccacgaaaaa acttcgtgaa gcctaatgag   5700

accaaaacat acttttggaa ggtgcagcac catatggccc caacaaaaga cgaattcgat   5760

tgcaaggcat gggcctattt ttctgacgtg gatctggaga aggacgtcca cagtggcctg   5820

atcgggccac tgctggtgtg tcatactaac accctgaatc ccgcacacgg caggcaggtc   5880

actgtccagg aattcgccct gttctttacc atctttgatg agacaaaaag ctggtacttc   5940

accgaaaaca tggagcgaaa ttgccgggct ccatgtaata ttcagatgga agaccccaca   6000

ttcaaggaga actaccgctt tcatgccatc aatgggtata ttatggatac tctgcccgga   6060

ctggtcatgg ctcaggacca gagaatcagg tggtacctgc tgagcatggg gtccaacgag   6120

aatatccact caattcattt cagcggacac gtgtttactg tccggaagaa agaagagtat   6180

aaaatggccc tgtacaacct gtatcccggc gtgttcgaaa ccgtcgagat gctgcctagc   6240

aaggcaggga tctggagagt ggaatgcctg attggggagc acctgcatgc cggaatgtct   6300

accctgtttc tggtgtacag taataagtgt cagacacccc tggggatggc ttccggacat   6360

atccgggatt tccagattac cgcatctgga cagtacggcc agtgggcccc taagctggct   6420

agactgcact attccgggtc tatcaacgct tggtccacaa aagagccttt ctcttggatt   6480

aaggtggacc tgctggcacc aatgatcatt catggcatca aaactcaggg ggccaggcag   6540

aagttctcct ctctgtacat ctcacagttt atcatcatgt acagcctgga tggcaagaaa   6600

tggcagacat accgcggcaa tagcacaggg actctgatgg tgttctttgg caacgtggac   6660

agttcaggga tcaagcacaa cattttcaat cccccctatca ttgctagata catcaggctg   6720

cacccaaccc attattctat tcgaagtaca ctgcggatgg aactgatggg gtgcgatctg   6780

aacagttgtt caatgcccct gggaatggag tccaaggcaa tctctgacgc ccagattacc   6840

gctagctcct acttcactaa tatgtttgct acctggagcc cctccaaagc acgactgcat   6900

ctgcagggac gaagcaacgc atggcgacca caggtgaaca atcccaagga gtggctgcag   6960

gtcgattttc agaaaactat gaaggtgacc ggagtcacaa ctcagggcgt gaaaagtctg   7020

ctgacctcaa tgtacgtcaa ggagttcctg atctctagtt cacaggacgg ccaccagtgg   7080

acactgttct ttcagaacgg aaaggtgaaa gtcttccagg gcaatcagga ttcctttaca   7140

cctgtggtca actctctgga cccacccctg ctgactcgct acctgcgaat ccacccacag   7200

tcctgggtgc atcagattgc actgagaatg gaagtcctgg gctgcgaggc ccaggacctg   7260

tattgattct aggctttgca agtatttcta acgcggccgc aggaacccct agtgatggag   7320
```

```
ttggccactc cctctctgcg cgctcgctcg ctcactgagg ccgggcgacc aaaggtcgcc   7380

cgacgcccgg gctttgcccg ggcggcctca gtgagcgagc gagcgcgcag ctgcctgcag   7440

gggcgcctga tgcggtattt tctccttacg catctgtgcg gtatttcaca ccgcatacgt   7500

caaagcaacc atagtacgcg ccctgtagcg gc                                 7532


<210> SEQ ID NO 5
<211> LENGTH: 21
<212> TYPE: DNA
<213> ORGANISM: Artificial Sequence
<220> FEATURE:
<223> OTHER INFORMATION: gRNA

<400> SEQUENCE: 5

gttagaaata cttgcaaagc c                                               21


<210> SEQ ID NO 6
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: n may be a, g, t, or c.
<220> FEATURE:
<221> NAME/KEY: misc_feature
<222> LOCATION: (9)..(20)
<223> OTHER INFORMATION: n is a, g, t, or c.
<220> FEATURE:
<221> NAME/KEY: misc_feature
<222> LOCATION: (21)..(22)
<223> OTHER INFORMATION: n can be any nucleotide.
<220> FEATURE:
<221> NAME/KEY: misc_feature
<222> LOCATION: (27)..(27)
<223> OTHER INFORMATION: w is a or t.

<400> SEQUENCE: 6

nnnnnnnnnn nnnnnnnnnn nnagaaw                                         27


<210> SEQ ID NO 7
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, g, t, or c.
<220> FEATURE:
<221> NAME/KEY: misc_feature
<222> LOCATION: (13)..(14)
<223> OTHER INFORMATION: n can be any nucleotide.
<220> FEATURE:
<221> NAME/KEY: misc_feature
<222> LOCATION: (19)..(19)
<223> OTHER INFORMATION: w is a or t.

<400> SEQUENCE: 7

nnnnnnnnnn nnnnagaaw                                                  19
```